US006117678A

United States Patent [19]
Carpenter et al.

[11] Patent Number: 6,117,678
[45] Date of Patent: *Sep. 12, 2000

[54] METHOD FOR DETERMINING MATURITY OF CONIFER SOMATIC EMBRYOS

[75] Inventors: Carolyn V. Carpenter; Martha K. Koester, both of Seattle; Pramod K. Gupta, Federal Way, all of Wash.

[73] Assignee: Weyerhaeuser Company, Federal Way, Wash.

[*] Notice: This patent issued on a continued prosecution application filed under 37 CFR 1.53(d), and is subject to the twenty year patent term provisions of 35 U.S.C. 154(a)(2).

[21] Appl. No.: 09/450,836

[22] Filed: Nov. 29, 1999

Related U.S. Application Data

[62] Division of application No. 09/064,887, Apr. 20, 1998, abandoned.
[60] Provisional application No. 60/044,114, Apr. 21, 1997, abandoned, and provisional application No. 60/068,688, Dec. 24, 1997, abandoned.

[51] Int. Cl.[7] .................................................. C12N 5/04
[52] U.S. Cl. ................... 435/422; 435/430; 435/430.1; 435/4
[58] Field of Search .................................. 435/422, 430, 435/430.1, 4

[56] References Cited

U.S. PATENT DOCUMENTS

| | | |
|---|---|---|
| 4,957,866 | 9/1990 | Gupta et al. . |
| 5,034,326 | 7/1991 | Pullman et al. . |
| 5,036,007 | 7/1991 | Gupta et al. . |
| 5,183,757 | 2/1993 | Roberts . |
| 5,187,092 | 2/1993 | Uddin . |
| 5,413,930 | 5/1995 | Becwar et al. . |
| 5,464,769 | 11/1995 | Attree et al. . |
| 5,506,136 | 4/1996 | Becwar et al. . |

OTHER PUBLICATIONS

Amuti, K. S. and C. J. Pollard. Soluble carbohydrates of dry and developing seeds. *Phytochemistry* 16: 529–532 (1977).

Attree, S. M., D. Moore, V. K. Sawhney, and L. C. Fowke. Enhanced maturation and desiccation Tolerance of white spruce [*Picea glauca* (Moench) Voss] somatic embryos: effects of a non–plasmolysing water stress and abscisic acid. *Annals of Botany* 68: 519–525 (1991).

Attree, S. M., M. K. Pomeroy, and L. C. Fowke. Development of white spruce (*Picea glauca* (Moench.) Voss) somatic embryos during culture with abscisic acid and osmoticum, and their tolerance to drying and frozen storage. *Journal of Experimental Botany* 46: 285, 433–439 (1995).

Bailey, P. C., G. W. Lycett, and J. A. Roberts. A molecular study of dormancy breaking and germination in seeds of *Trollius ledebouri*. *Plant Molecular Biology* 32: 559–564 (1996).

Barnett, J. P. Cone and seed maturation of southern pines. U.S. Department of Agriculture Forest Research Paper SO–122 (1976).

Barnett, J. P. and A. W. Naylor. Respiratory and biochemical changes during germination of longleaf and slash pine seeds. *Forest Science* 16 (3): 350–355 (1970).

Bernal–Lugo, I. and A. C. Leopold. Changes in soluble carbohydrates during seed storage. *Plant Physiology* 98: 1207–1210 (1992).

Black, M., F. Corbineau, M. Grzesik, P. Guy, and D. Côme. Carbohydrate metabolism in the developing and maturing wheat embryo in relation to its desiccation tolerance. *Journal of Experimental Botany* 47 (295): 161–169 (1996).

Blackman, S. A., S. H. Wettlaufer, R. L. Obendorf, and A. C. Leopold. Maturation proteins associated with desiccation tolerance in soybean. *Plant Physiology* 96: 868–874 (1991).

Blackman, S. A., R. L. Obendorf, and A. C. Leopold. Maturation proteins and sugars in desiccation tolerance of developing soybean seeds. *Plant Physiology* 100: 225–230 (1992).

Bradford, Kent J. A water relations analysis of seed germination rates. *Plant Physiology* 94: 840–849 (1990).

Brenac, P., M. Horbowicz, S. M. Downer, A. M. Dickerman, M. E. Smith, and R. L. Obendorf. Raffinose accumulation related to desiccation tolerance during maize (*Zea mays* L.) seed development and maturation. *Journal of Plant Physiology* 150: 481–488 (1997).

Castillo, Eugenia M., B. O. de Lurnen, P. S. Reyes, and H. Z. de Lumen. Raffinose synthase and galactinol synthase in developing seeds and leaves of legumes. *Journal of Agricultural and Food Chemistry* 38: 351–355 (1990).

Ching, T. M. Change of chemical reserves in germinating Douglas–fir seed. *Forest Science* 9 (2): 226–23 1 (1963).

Ching, T. M. Compositional changes of Douglas fir seeds during germination. *Plant Physiology* 41: 1313–1319 (1966).

Close, T. J., R. D. Fenton, and F. Moonan. A view of plant dehydrins using antibodies specific to the carboxy terminal peptide. *Plant Molecular Biology* 23: 279–286 (1993).

Dahal, P., N–S. Kim, and K. J. Bradford. Respiration and germination rates of tomato seeds at suboptimal temperatures and reduced water potentials. *Journal of Experimental Botany* 47: 941–947 (1996).

(List continued on next page.)

*Primary Examiner*—Leon B. Lankford, Jr.

[57] ABSTRACT

The invention concerns measurement of sucrose series oligosaccharides, particularly sucrose, raffinose, and stachyose, and the dehydrin group proteins, in conifer somatic embryos as a measure of their biochemical maturity and readiness to germinate. The information gained is useful for evaluation of the effectiveness of the culture media, particularly that used for the development of the cotyledonary embryo stage. Somatic embryos having elevated levels of the oligosaccharides have been shown to have improved germination, especially those in the genus Pinus. The invention is also directed to conifer somatic embryos having elevated levels of sucrose series oligosaccharides and dehydrin group proteins.

5 Claims, 8 Drawing Sheets

OTHER PUBLICATIONS del Mar Parra, M., O. del Pozo, R. Luna, J. A. Godoy, and J. A. Pintor–Toro. Structure of the dehydrin tas14 gene of tomato and its developmental and environmental regulation in transgenic tobacco. *Plant Molecular Biology* 32: 453–460 (1996).

Demir, I. and R. H. Ellis. Changes in seed quality during seed development and maturation in tomato. *Seed Science Research* 2: 81–87 (1992).

Dure III, L., M. Crouch, J. Harada, T–H. D. Ho, J. Mundy, R. Quatrano, T. Thomas, and Z. R. Sung. Common amino acid sequence domains among the LEA proteins of higher plants. *Plant Molecular Biology* 12: 475–486 (1989).

Durzan, D. J. and V. Chalupa. Free sugars, amino acids, and soluble proteins in the embryo and female gametophyte of jack pine as related to climate at the seed source. *Canadian Journal of Botany* 46: 417–428 (1968).

East, J. W., T. O. M. Nakayama, and S. B. Parkman. Changes in stachyose, raffi–nose, sucrose and monosaccharides during germination of soybeans. *Crop Science* 12: 7–9, (Jan.–Feb. 1972).

Ellis, R.H. and E. H. Roberts. Improved equations for the prediction of seed longevity. *Annals of Botany* 45: 13–30 (1980).

Finkelstein, R. R., and M. L. Crouch. Precociously germinating rapeseed embryos retain characteristics of embryogeny. *Planta* 162: 125–131 (1984).

Frias, J., C. Vidal–Valverde, H. Kozlowska, R. Gorecki, J. Honke, and C L. Hedley. Evolution of soluble carbohydrates during the development of pea, fava bean and lupin seeds. *Z. Lebensm. Unters. Forch.* 203: 27–32 (1996).

Galau, G. A., K. S. Jakobsen, and D. W. Hughes. The controls of late dicot embryogenesis and early germination. *Physiologia Plantarum* 81: 280–288 (1991).

Han, B., D. W. Hughes, G. A. Galau, J. D. Bewley, and A. R. Kermode. Changes in late embryogenesis abundant (LEA) messenger RNAs and dehydrins during maturation and premature drying of *Ricinus communis* L. seeds. *Planta* 201: 27–35 (1997).

Han, B. and A. R. Kermode. Dehydrin–like proteins in castor bean seeds and seedlings are differentially produced in response to ABA and water–deficit–related stresses. *Journal of Experimental Botany* 47 (300): 933–939 (1996).

Handley, L. W., D. M. Pharr, and R. F. McFeeters. Relationship between galactinol synthase activity and sugar composition of leaves and seeds of several crop species. *Journal of American Society of Horticultural Science* 108 (4): 600–605 (1983).

Hattori, S and T. Shiroya. The sugars in the seeds and seedlings of *Pinus thunbergii*. *Archives of Biochemistry and Biophysics* 34: 121–134 (1951).

Hurkman, W. J. and C. K. Tanaka. Effect of salt stress on germin gene expression in barley roots. *Plant Physiology* 110 (3): 971–977 (1996).

Jakobsen, K. S., D. W. Hughes, and G. A. Galau. Simultaneous induction of postabscission and germination mRNAs in cultured dicotyledonous embryos. *Planta* 192: 384–394 (1994).

Jarvis, S. B., M. A. Taylor, J. Bianco, F. Corbineau, and H. V. Davies. Dormancy–breakage in seeds of Douglas–fir (*Pseudotsuga menziesii* (Mirb.) Franco). Support for the hypothesis that LEA gene expression is essential for this process *Journal of Plant Physiology* 151: 457–464 (1997).

Jarvis, S. B., M. A. Taylor, M. R. MacLeod, and H. V. Davies. Cloning and characterisation of the cDNA clones of three genes that are differentially expressed during dormancy–breakage in the seeds of Douglas–fir (*Pseudotsuga menziesii*). *Journal of Plant Physiology* 147: 559–566 (1996).

Kao, C. Biochemical changes in seeds of Taiwan red pine and Chinese fir during germination. *Forest Science* 19 (4): 297–301 (1973).

Kardell, L., B. Nyman, and S. Bobeck. Ripening process in relation to temperature and sugar content in seeds of Scots pine (*Pinus sylvestris* L.). *Studia Forestalia Suecica*, No. 107 (1973).

Koster, K. L. and A. C. Leopold. Sugars and desiccation tolerance in seeds. *Plant Physiology* 88: 829–832 (1988).

Kuo, T. M., C. A. Lowell, and P. T. Smith. Changes in soluble carbohydrates and enzymatic activities in maturing soybean seed tissues. *Plant Science* 125: 1–11 (1997).

Kuo, T. M., J. F. VanMiddlesworth, and W. J. Wolf. Content of Raffinose Oligosaccharides and Sucrose in Various Plant Seeds. *Journal of Agricultural and Food Chemistry* 36: 32–36 (1988).

Leprince, O., G. A. F. Hendry, and B. D. McKersie. The mechanisms of desiccation tolerance in developing seeds. *Seed Science Research* 3: 231–246 (1993).

Lin, T–P. and N–H. Huang. The relationship between carbohydrate composition of some tree seeds and their longevity. *Journal of Experimental Botany* 45 (278): 1289–1294 (1994).

Lowell, C. A. and T. M. Kuo. Oligosaccharide metabolism and accumulation in developing soybean seeds. *Crop Science* 29: 459–465 (1989).

Liu, W., D. F. Hildebrand, P. J. Moore, and G. B. Collins. Expression of desiccation–induced and lipoxygenase genes during the transition from the maturation to the germination phases in soybean somatic embryos. *Planta* 194: 69–76 (1994).

Misra, S. and M. Green. Legumin–like storage polypeptides of conifer seeds and their antigenic cross–reactivity with 11 S globulins from angiospernis. *Journal of Experimental Botany* 45 (271): 269–274 (1994).

Murphy, J. B. and M. F. Hammer. Respiration and soluble sugar metabolism in sugar pine embryos. *Physiologia Plantarum* 74: 95–100 (1988).

Ni, B–R. and K. J. Bradford. Quantitative models characterizing seed germination responses to abscisic acid and osmoticurn. *Plant Physiology* 98: 1057–1068 (1992).

Nyman, B. Studies on sugars and starch in light– and dark–germinated seeds of Scots pine (*Pinus silvestris*). *Physiologia Plantarum* 22: 441–452 (1969).

Owens, J. N., S. J. Morris, and S. Misra. The ultrastructural, histochemical, and biochemical development of the post–fertilization megagametophyte and the zygotic embryo of *Pseudotsuga menziesii*. *Canadian Journal of Forestry Research* 23: 816–827 (1993).

Rediske, J. H. Effects of cone–picking date on Douglas–fir seed quality. *Forest Science* 15 (4): 404–410 (1969).

Roberts, D. R., B. C. S. Sutton, and B. S. Flynn. Synchronous and high frequency germination of interior spruce somatic embryos following partial drying at high relative humidity. *Canadian Journal of Botany* 68: 1086–1090 (1990).

Rosenberg, L. A. and R. W. Rinne. Moisture loss as a prerequisite for seedling growth in soybean seeds (*Glycine max* L. Merr.). *Journal of Experimental Botany* 37 (184): 1663–1674 (1986).

Rosenberg, L. A. and R. W. Rinne. Protein synthesis during natural and precocious soybean seed (*Glycine max* [L.] Merr.) maturation. *Plant Physiology* 87: 474–478 (1988).

Schneider, W. L. and D. I Gifford. Loblolly pine seed dormancy. 1. The relationship between protein synthesis and the loss of dormancy. *Physiologia Plantarum* 90: 246–252 (1994).

Steadman, K. J., H. W. Pritchard, and P. M. Dey. Tissue–specific soluble sugars in seeds as indicators of storage category. *Annals of Botany* 77: 667–674 (1996).

Taylor, M. A., H. V. Davies, S. B. Smith, A. Abruzzese, and P. G. Gosling. Cold induced changes in gene expression during dormancy breaking in seeds of Douglas–fir (*Pseudotsuga menziesii*). *Journal of Plant Physiology* 142: 120–123 (1993).

Walters–Vertucci, C., J. Crane and N. C. Vance. Physiological aspects of *Taxus brevifolia* seeds in relation to seed storage characteristics. *Physiologia Plantarum* 98: 1–12 (1996).

Wisniewski, M., T. J. Close, T. Artlip, and R. Arora. Seasonal patterns of dehydrins and 70–kDa heat shock–proteins in bark tissues of eight species of woody plants. *Physiologia Plantarum:* 96: 496–505 (1996).

Wood, A. J. and P. B. Goldsbrough . Characterization and expression of dehydrins in water–stressed *Sorghum bicolor. Physiologia Plantarum* 99: 144–152 (1997).

METHOD FOR DETERMINING MATURITY OF CONIFER SOMATIC EMBRYOS

This application is a divisional application of Ser. No. 09/064,887, filed Apr. 20, 1998 now abandoned and also claims priority from provisional applications Ser. No. 60/044,114, filed Apr. 21, 1997 now abandoned and Ser. No. 60/068,688, filed Dec. 24, 1997.

The present invention is concerned with maturation of conifer somatic embryos in tissue culture and with the embryos so produced. It also concerns determination of somatic embryo biochemical maturity by analysis of simple sugars, oligosaccharides and certain protein compounds of the dehydrin group.

BACKGROUND OF THE INVENTION

As forests around the world have become depleted by logging for lumber, fuel, and land expansion, intensively managed tree plantations in the world's developed countries have become the major source for the world's sustainable supply of soft-woods. About eight species now comprise the great bulk of the plantation wood presently being grown worldwide. The predominant species in North America is usually one that is native to the region. In other areas of the world it is more typically an exotic that has proved particularly well adapted to the locale. The Monterey pine (*Pinus radiata* Don.) grown widely in Africa, Australia and New Zealand is an example of an exotic species which grows particularly well in a non-native locale.

Genetic selection of the plantation species has resulted in trees having heritable improvements in a number of regards in comparison with those found in natural stands. Rapid growth to harvestable size has been the principal improvement sought. This selection process has been so successful that in some areas rotations as low as 25 years are standard. Virtually all plantations are now restocked with seedlings grown from seed obtained from what in many cases is third generation seed orchards, In recent years large numbers of rooted cuttings from young trees originating from genetically select seed have also become an important source for restocking programs. This is one way of bulking up scarce and expensive full sib seed.

Rooted cuttings are an example of forestry where, on a small scale, the characteristics of selected parents are passed on intact to a succeeding generation. They have the disadvantage of being quite expensive in comparison with natural seedlings. For the past two decades research has been conducted on reproduction of conifers by tissue culture as a method of producing select clonal stock. This method is just now in its commercial infancy. The process most widely employed is embryogenesis. An embryo from a desirable seed is placed on a culture medium where multiple early stage genetically identical replicates are produced. Immature early stage embryos are placed on a series of media where they are further multiplied and cultured to a mature state where they are morphologically similar to zygotic embryos. These newly grown somatic embryos may then be placed on a germination medium for conversion into plants. Alternatively, they may be formed into manufactured seeds.

Some examples showing conifer embryogenesis procedures are found in U.S. Pat. Nos. 4,957,866, and 5,036,007 to Gupta et al., U.S. Pat. No. 5,034,326 to Pullman et al., U.S. Pat. No. 5,563,061 to Gupta, U.S. Pat. No. 5,413,930 and U.S. Pat. No. 5,506,136 to Becwar et al. and U.S. Pat. No. 5,187,092 to Uddin.

During the earlier tissue culture efforts the embryos produced had a very low success rate for conversion into rooted plants. This remains a problem today although the current success rate is much higher. However, the important Pine species have been particularly intractable. In the effort to increase successful conversion, much attention was given to culture conditions attempting to improve the morphology of the somatic embryos so that they physically resembled zygotic embryos as closely as possible. Various changes were made in the culture media nutrients and hormones to effect these improvements. Unfortunately, a high degree of morphological resemblance did not ensure good germination and conversion. More recently, investigators have studied the importance of storage products in somatic embryos as they relate to germination success and resulting plant vigor. Storage products are generally defined as lipids and proteins found within the embryo and in the surrounding megagametophyte of a natural seed. Some authorities in the field would also include carbohydrates as a component of storage products.

Storage products provide the initial energy needed upon germination. Additionally, the storage products may be associated with desiccation tolerance in embryos. One example of the importance placed on high levels of stored lipids in somatic embryos can be found in U.S. Pat. No. 5,464,769 to Attree et al.

In the discussion that follows, reference to journal articles are noted only by lead author and date. Reference should be made to the bibliography following the specification for full citations.

The biochemical changes that occur within developing somatic embryos are extremely complex and are still poorly understood. In addition to the lipid and proteinaceous materials, the carbohydrates now appear to have a critically important role. These have been studied for a number of species. Steadman et al. (1996) studied development of soluble sugars in a broad spectrum of angiosperm species. In particular, they looked at differences between "orthodox" seeds having high germination success and "recalcitrant" seeds which had poor germination. They found that orthodox seeds generally had significantly higher ratios of the oligosaccharides raffinose and stachyose to sucrose at maturity. Frias et al. (1996) studied three legume species. They noted that simple sugars decreased during seed development and raffinose, stachyose and verbascose appeared later as the seed matured. They did not specifically study embryos and found significant differences between species. Black et al. (1996), reported their work with development of wheat embryos. An early starch accumulation declined to a very low value at maturation Sucrose and raffinose continued to increase during maturation, the major increase in raffinose approximating the time of the fall in starch content. The development of desiccation tolerance was associated with increasing raffinose to sucrose ratios. Bernal-Lugo et al. (1992), note that depletion of raffinose in aged corn is related to a decline in seed vigor.

Workers in the field of tissue culture learned early on that it was an inexact and unpredictable science. What worked for one genus failed for another. Often what worked for one species failed for a closely related species within the same genus. The correspondence gap has been particularly wide between the angiosperms and gymnosperms. To the present inventors' knowledge similar studies to those noted above on embryo development have not been carried out on the gymnosperm species within the botanical Order Coniferales. Studies of sugar content and metabolism have been carried out later in the process; i.e., on germinating seeds. Hattori et al. (1951) note the presence of sucrose, raffinose, and stachyose in mature seeds of *Pinus thunbergii*. As the tip of the young root appeared the raffinose and stachyose rapidly disappeared. Durzan et al (1968) examined the above three sugars and free amino acids in the embryos and female gameteophytes of jack pine (*Pinus banksiana* Lamb.). Geographic source of the seed introduced considerable variation in both the absolute levels of the three sugars as well as the respective ratios of the higher oligosaccharides to sucrose. Murphy et al. (1988) reported the levels of soluble sugars and hydrolytic enzymes as related to the release of dormancy and germination for sugar pine (*Pinus lambertiana* Dougl.). They noted that on germination, raffinose and stachyose dropped steadily to very low levels over about 15 days. Sucrose rose to a sharp peak at about 7 days then began a marked decline. Lin et al. (1994), in a study of 17 species including four Asiatic conifers, concluded that the ratio of oligosaccharide to disaccharide plays a role in desiccation tolerance and longevity of orthodox seeds. They note that the accumulation of the raffinose series of sugars is induced by slow drying during seed maturation but that the ratio between raffinose and stachyose is probably species dependent. Similarly, Leprince et al. (1993) state that oligosaccharides are important in cell wall protection of angiosperms during desiccation but conclude that they are only one of a suite of important and interrelated factors. Ching (1966) looked at the compositional changes in Douglas-fir during germination and concluded that the metabolic changes observed were similar to angiosperm seeds. Kao (1973) studied germination of Taiwan red pine (*Pinus taiwanensis* Hayata) and Chinese fir (*Cunninghamia lanceolata* (Lamb) Hook.) with the conclusion that fats were the main reserve materials. He noted that sucrose, raffinose and stachyose occurred in non-germinated seed of red pine while the oligosaccharides were replaced by fructose and glucose in germinated seeds. Raffinose, sucrose, fructose and glucose were found in both non-germinated and germinated seed of Chinese fir.

In addition to the di- and oligosaccharides formed in developing embryos, a group of extremely hydrophilic, heat-soluble proteins with no enzyme activity called Late Embryogenesis Abundant (LEA) proteins accumulates in plant embryos (Dure et al. 1989). Within this group of proteins is a family generally termed "dehydrins" (Close et al. 1993). Genes for dehydrins are expressed (1) naturally during seed development (Close et al. 1993); (2) in response to cold and water stress (Hurkman et al. 1996; Wisniewski et al. 1996); and (3) in response to the phytohormone abscisic acid (ABA). Although both ABA and water stress play important roles during seed development, it is not clear what signal induces the synthesis of dehydrin during seed development in situ (Han et al 1996: Wood et al. 1997).

Neither is the function of the LEA family of proteins entirely clear. But, because of its pattern of expression, it is thought to be involved in stress tolerance. Nevertheless, attempts to define a precise function in tolerance to desiccation or cold have proven fruitless and the search for function still goes on. In angiosperm zygotic embryos, dehydrin proteins accumulate during late embryogenesis—after the major period of reserve deposition is completed (Han et al. 1997). They can also be prematurely induced under a variety of conditions upon excision of young embryos from the mother plant (Galau et al. 1991).

Germination of embryos is an outcome of cell expansion and cell division. The first visible sign of germination in isolated embryos is axis elongation (radicle+hypocotyl+ epicotyl). After an embryo is placed in an environment with a water potential high enough to support germination (greater than about −2.0 MPa) it hydrates to a certain water content. No further visible changes occur until germination itself The period between placing the embryo on water and visible germination is referred to as "lag time". In a mature seed of a given species, the length of the lag time can be closely predicted. It depends on water potential, endogenous ABA, and temperature. It may be that certain biochemical events must occur before cell expansion leading to germination can occur and that the rate of these biochemical events depends on water content and temperature. Respiratory rate during this time is a function of water content, temperature, and time. It has been noted that respiratory rate increases with imbibition time. However, respiration appears to be indicative of biochemical reaction in general rather than causative of germination. From the fact that respiration and utilization of stored reserve products occurs during the lag phase, it follows that the longer the lag phase at a given temperature and water content, the less stored reserves remain for early seedling growth.

If embryos or seeds are excised before a critical point in their development they may not germinate at all. If they do, they do so slowly and often exhibit abnormalities (e.g., see Blackman et al. 1992). An unusually long lag time contributes to the poor vigor in these cases. It seems reasonable that the young embryos are using this lag time to complete some unfulfilled biochemical process that is essential for them to become germinable—a process that would have otherwise occurred had they been left to complete their normal development on the mother plant.

A candidate for this putative process is protein synthesis. Gene expression studies show that when immature angiosperm embryos of a number of species are excised and placed on nutrient medium, two groups of proteins are synthesized (Jacobsen et al. 1994). One group, consisting of enzymes for reserve breakdown, is characteristic of germination. The other group is the LEA proteins. Concomitant with the synthesis of these proteins, storage proteins are catabolized.

The co-expression of two developmental programs that are normally temporally distinct during zygotic embryogenesis may have profound implications for the vigor of the germinant. If certain developmental events must be completed before germination can occur, then it is likely that the prolonged lag phase in immature embryos reflects the time necessary to complete these events. However, if germination (at least in the sense of reserve breakdown) starts before these events are completed, the embryo, when it is finally ready to germinate, is left with less "fuel" for subsequent growth since it was used during the prolonged lag phase. Left to develop on the plant, the continuous withdrawal of water from the system ensures that the required developmental events will be completed in a timely manner without the premature onset of germination.

It has been frequently shown that incubating young embryos at a water potential that does not permit germination, but is still high enough to permit biochemical activity, decreases the lag time so that it approaches that of mature embryos (e.g., see Blackman et al. 1992). During this time specific proteins are synthesized including heat soluble proteins and dehydrin (Han et al. 1997). Incubation at high R.H., causing a concomitant slow drying, has also been shown to enhance germinability in gymnosperm somatic embryos, (e.g., Roberts, U.S. Pat. No. 5,183,757, Roberts et al. 1990). One might also predict that the slightly lowered water potential prevents the hydrolysis of reserves that would occur at higher water potentials so that the embryos can complete the developmental steps necessary for germination without compromising their reserve status.

The heat soluble proteins, including dehydrin, that are abundant during maturation and quiescence are rapidly broken down during germination whether the embryos are naturally matured or prematurely dried. The tight link between quiescence or dormancy and the presence of dehydrin has been noted both in seeds and non-seed dormant tissue such as overwintering buds (Wisniewski et al. 1996).

In zygotic embryogenesis, "maturity" is easy to identify because the seed dries and dehisces from the mother plant Shortly after the onset of drying the zygotic embryo attains maximum germinability. Essentially, the pre-programmed development and environmental responses of the embryo and mother plant dictate maturity. We are left simply to harvest the mature seed and treat it optimally after harvest. However, this is not the case with somatic embryos where scientists must dictate the timing and protocol of every shift in hormones, media composition, water potential, photoperiod, and temperature. In somatic embryos, the period of quiescence which so clearly demarcates maturation from germination in zygotic embryogenesis is completely lacking. Morphological maturity based on appearance has heretofore been used as a criterion but this crude tool has proved to be highly undependable. Other tools or markers which would serve in its stead, to signal the achievement of maximum maturity and readiness for germination, have heretofore been lacking.

The requirements of an embryo during maturation are completely different and virtually opposite to the requirements of an embryo during germination. Morphology is the outcome or result of changes that have taken place at the biochemical level. However, it does not reveal all of them, particularly at this critical juncture between biochemical maturity and readiness to germinate. More precise biochemical tools to signal these changes would be extremely helpful to the scientists working with somatic embryogenesis. It would allow them to precisely identify needed protocol changes and the timing of their imposition.

None of the investigators working on conifer tissue culture appear to have looked at the development over time of the more complex sugars in maturing somatic embryos nor has the importance of this been recognized. Neither do they have seemed to study in any detail the development of the dehydrin protein group and its importance.

SUMMARY OF THE INVENTION

The present invention is concerned with using knowledge of the simple sugar and sucrose series oligosaccharide content of coniferous embryos as a marker indicator of their biochemical maturity. It is particularly useful as a tool in tissue culture methods employing somatic embryogenesis for indicating when embryo development is complete.

The method is based on the discovery that the morphological maturity of zygotic embryos of the coniferous species investigated occurs at a significant period of time before their apparent biochemical maturity.

The invention further recognizes the importance of dehydrin group proteins in somatic embryos as an indicator of readiness to germinate and the presence of dehydrin decomposition compounds as indicators of the onset of germination.

As was noted earlier, gross morphology has to date been the principal indicator of somatic embryo maturity. A set of visual criteria has been developed for selection of mature embryos likely to have a high conversion rate into plants. Among several other features, the embryo must have well developed cotyledon primordia, a smooth hypocotyl, and be radially symmetrical. Color must be within predetermined standards and a defined list of abnormalities must be absent. It is understood that histological sections of representative embryos should have close resemblance to their zygotic counterparts. However, it has been a source of frustration that robust embryos from different cultures that looked essentially identical often performed very differently in regard to such criteria as longevity, desiccation tolerance and germination success. Further, it has sometimes been very difficult to judge the effects of different media compositions that produce visually similar embryos until time consuming extensive downstream evaluation has been carried out.

It has now been shown that sugar analysis can be a helpful indicator of biochemical maturity in addition to selection based solely on morphological characteristics. Work has been conducted on two disparate coniferous species examining sugar development in zygotic (seed) embryos as cones mature on trees. Similar patterns have been found on Douglas-fir (*Pseudotsuga menziesii* (Mirb.) Franco) and Loblolly pine (*Pinus taeda* L.). Data on a third species, white spruce (*Picea glauca* (Moench) Voss.), is presently limited to mature embryos but the data overall are so consistent that more general conclusions may be drawn.

Douglas-fir can be taken as one example. Anatomical and morphological seed embryo maturity of this species in the United States Pacific Northwest normally is complete in August. No further morphological change with time is evident in the embryos. However, the complex sugars, raffinose and stachyose, are still in very low concentration at that time and do not peak until about a month later. Sucrose also continues to rise to a peak in September. The simple sugars glucose and fructose show a significant drop during the same period. Experience has shown September to be the optimum harvest time for cones taken from seed orchards.

It has now been discovered that the presence of elevated concentrations of sucrose series oligosaccharides and the presence of the dehydrin group proteins appears be highly beneficial in somatic embryos for good germination and conversion into plants. It is believed that these same sugars are important in somatic embryos for imparting desiccation tolerance, a necessity for some types of manufactured seed. Somatic embryo quality appears to improve significantly with increasing levels of the sucrose series oligosaccharides and the dehydrin group proteins.

The sucrose series of oligosaccharides comprises, sucrose, raffinose, stachyose, and verbascose. These are nonreducing, water soluble, sucrosyl series saccharides. Each are based on sucrose with the other three members having respectively one, two, and three galactose units attached. Verbascose is not usually found in significant amounts in conifer embryos. Desirable combined values of raffinose and stachyose are at least about 4 nanomoles/mg of dry embryo weight. Similarly, it is preferred that sucrose should also be present in an amount of at least about 125 nanomoles/mg of embryo dry weight.

Sugar and protein analysis has also been shown to be highly beneficial in distinguishing differences in morphologically similar embryos matured on different culture media. Thus this serves as a new and valuable analytical tool which has not heretofore been used to guide the investigator in formulating optimum culture media for development of somatic embryos.

It is therefore an object of the invention to provide a method for attaining and evaluating biochemical maturity of somatic embryos.

It is another object to provide somatic embryos having high levels of essential complex sugars whereby they have improved germinability and desiccation tolerance.

It is still an object to provide a method for culture of somatic embryos having high viability.

It is a further object to provide a method for evaluating the effectiveness of culture media used for development of somatic embryos.

It is yet an object to provide a method for determining when somatic embryos have reached maturity and are ready to germinate.

It is also an object to provide a method for indicating when germination has commenced.

It is an additional object to provide somatic embryos with elevated levels of the dehydrin group proteins.

These and many other objects will become readily apparent upon reading the following detailed description taken in conjunction with the drawing.

DETAILED DESCRIPTION OF THE PREFERRED EMBODIMENTS

Figure 1:
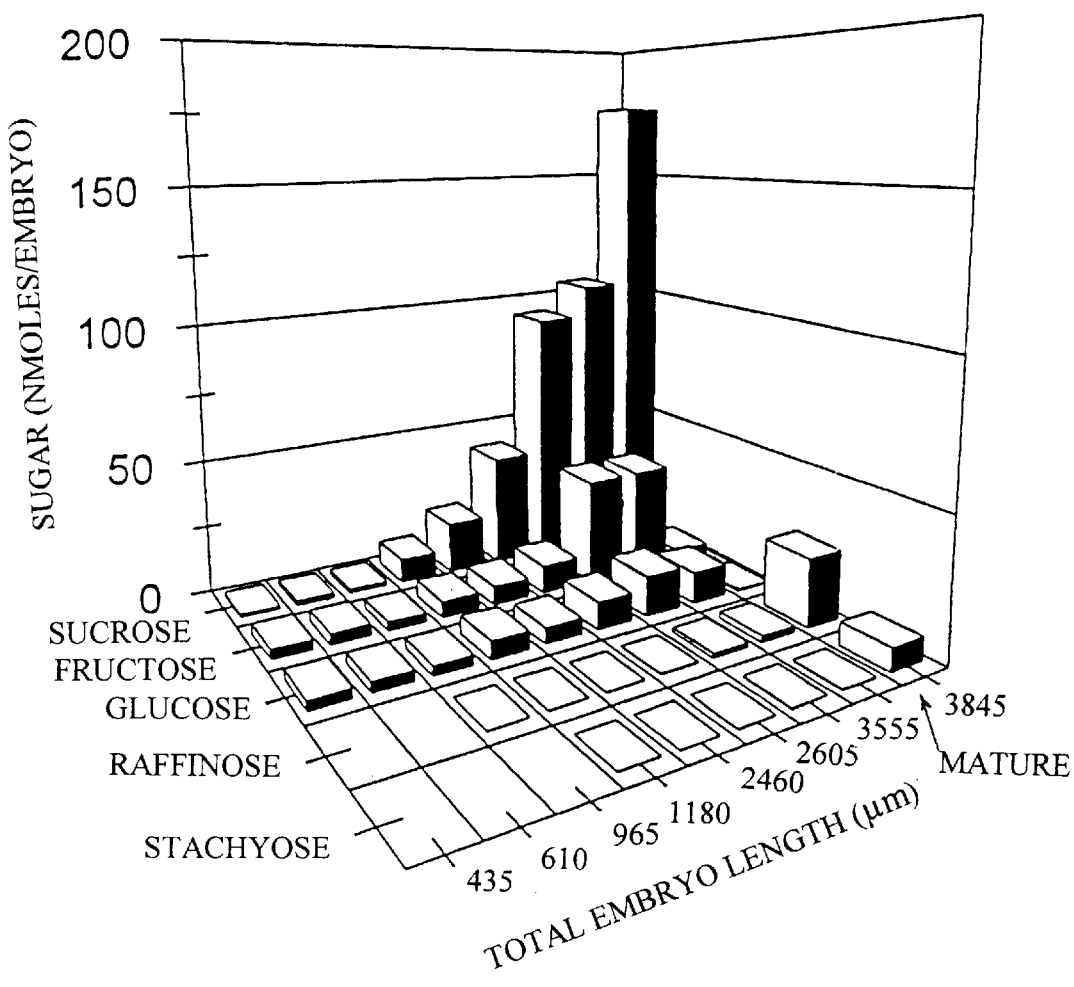
FIG. 1 is a three dimensional bar graph showing accumulation over time of soluble simple and complex sugars during the development of zygotic Douglas-fir embryos.

Protocols for successful somatic embryogenesis of gymnosperms, especially trees in the Order Coniferales, is well established for a significant number of species. These procedures are well described in the scientific and patent literature. In particular, trees in the genera Picea, Pseudotsuga, and Pinus have received extensive study since they include most of the world's commercially important softwood species. However, the transition from a somatic embryo in a Petri dish to a tree growing in the forest has not had the same measure of success. In many cases the somatic embryos either fail completely to germinate, germinate precociously before they are fully developed, or form morphologically abnormal plantlets. In particular, the pines have resisted satisfactory germination to plants growing in soil on any but the smallest scale.

Certain attributes of somatic embryos are known to be essential if successful germination is to be achieved. "Successful", as used here, means germination into a normal plant capable of survival and growth typical of the species when outplanted. Among these embryo attributes are possession of essential organ primordial e.g., root and shoot apical meristems, as well as some as yet poorly defined level of storage reserves. The term "storage reserves" as used here would broadly include the proteins, lipids, and carbohydrate compounds essential for nutrition during germination and very early growth. To these known attributes may now be added the desirable presence of soluble proteins in the dehydrin group which are typically formed after the accumulation of storage reserves has essentially been completed. Up to this time dehydrins have not been recognized as being present in gymnosperm somatic embryos, much less as being important for normal germination. As was noted earlier, their presence is an indicator of readiness to germinate and their decomposition products are an indicator of the onset of germination.

In a study of oligosaccharide formation in natural seeds, full sib cones were periodically collected from a single tree in a Washington State Douglas-fir seed orchard. Collection began in early July, when the embryos were still in the pre-dome stage and was continued until the embryos were morphologically mature in early August. Due to a sampling error, the seed taken in September was collected from different trees in the same orchard.

Soluble sugars were determined in embryos by high pressure liquid chromatography (HPLC) coupled to a pulsed amperometric detector using standard published methods. Briefly, the embryos were extracted twice with 80% ethanol at 80° C. 5 $\mu$L $^{14}$C glucose ($2.2 \times 10^6$ dpm) was added to the pooled supernatant as an internal standard. The supernatant was evaporated to dryness at 35–40° C. and the dried sample was washed with ether to remove lipids. Then the ether washed sample was dissolved in 0.5 mL of ultrapure water. Duplicate 10 $\mu$L samples of the supernatant were taken and were counted in a scintillation counter. Radioactivity of these samples was compared with that in the original pooled supernatant to correct for any sample loss due to transfer from vessel to vessel. The remaining sample was used for the HPLC determination of sugars (see Handley et al. 1983).

The results for the Douglas-fir embryos are seen in FIG. 1. Up to the point of morphological maturity in August only simple sugars are present in significant quantities. Embryos have at this time attained their maximum average length of 3845 $\mu$m. Sucrose has been rising sharply, fructose has peaked, and glucose is falling. Raffinose and stachyose are present but in very small quantities. In the September sample, sucrose has climbed to a sharp peak as have raffinose and stachyose. The two simple sugars have dropped dramatically.

Similar embryo development behavior to the above has also been observed in loblolly pine. It is clear for all these species that biochemical maturity significantly lags morphological maturity in time.

SOMATIC EMBRYOGENESIS BY TISSUE CULTURE

In typical conifer tissue culture by somatic embryogenesis, an embryo, most usually selected from an immature seed, is placed on a gelled initiation medium for a period of time in the dark. The seed is sterilized, the seed coat removed, and the embryo may or may not be dissected from the female gametophyte before placing it on the initiation medium. Initiation media will normally have a finite concentration of the growth hormones classed as auxins and cytokinins. Initiation success may vary from as low as 1% or less of the initial cultures to over 10%. In successful cultures, within six to eight weeks a gelatinous mass will have formed containing many small early stage embryos, typically of ten or less cells. The gelatinous mass, widely referred to as an embryonal-suspensor mass or ESM, may then be removed from the initiation medium to a maintenance medium. For some species this may be a gelled medium for a short period followed by a gently agitated liquid medium. The maintenance media are usually of similar composition to the initiation medium but most frequently with significantly reduced growth hormones. The embryos in maintenance are subcultured to fresh media on a regular basis, usually at about two week intervals. For some species an optional treatment may follow with a medium having a raised osmotic level in order to produce larger early stage embryos. Also, specifically for Douglas-fir, a treatment may be used at this point to singulate any clumped embryos.

From the maintenance stage, embryo culture is then most usually directed to a development or growth medium where the early stage embryos advance to the cotyledonary embryo stage. This may be a gelled medium or the embryos may be placed on an absorbent pad kept wet in liquid medium. Auxins and cytokinins are absent and usually abscisic acid is a newly added hormone. Development to the morphologically mature stage usually occurs in about six to eight weeks.

Protocols and media composition for somatic embryogenesis are well documented for the various conifer species. As one example, U.S. Pat. No. 5,036,007 to Gupta and Pullman gives detailed procedures and media compositions for loblolly pine, Douglas-fir, and Norway spruce. Similarly, U.S. Pat. No. 5,563,061 to Gupta compares the effects of different sugars in maintenance media. Both patents are herein included in their entirety by reference. The following example describes the procedure used for Douglas-fir culture.

DOUGLAS-FIR CULTURE

EXAMPLE 1

A basal culture medium described in Table 1 has been developed specifically to give more successful initiation and multiplication of Douglas-fir. Preferred media compositions for the different culturing stages are given in Table 2. A number of ingredients may be varied in quantity, such as those that affect the level and balance between organic and inorganic nitrogen, depending on the response of individual genotypes. This response cannot be readily predicted and media optimization must largely be achieved by a combination of intuition and trial and error.

The embryogeny of Douglas-fir is quite different from trees such as the spruces or pines. One of these differences is seen when early stage embryos are placed in or on an advanced early stage embryo development medium. Instead of single advanced early stage embryos, Douglas-fir tends to develop tight clumps of these embryos. Upon further development into cotyledonary embryos, many of these clumps remain united and the resulting product is difficult to work with for further conversion. The present method utilizes a series of liquid shake cultures with reduced osmotic level and added abscisic acid between the advanced early stage embryo development and cotyledonary embryo development stages to achieve the necessary singulation. Osmotic level in the development medium is again raised to levels generally above about 450 mM/kg during the final cotyledonary embryo development stage or stages.

In addition to glucose, sucrose, or maltose, sorbitol (D-glucitol), D-mannitol, and galactitol (dulcitol) are straight chain sugar alcohols suitable for control of osmotic potential in the final development medium. Lactose is another sugar effective for the same purpose. Other synthetic materials suitable as osmoticants may include glycol ethers such as poly(ethylene glycol) and poly(propylene glycol) and their respective monomers. Mannitol, lactose, and the synthetic materials are not metabolizable by the developing embryos.

TABLE 1

*Pseudotsuga Menziesii* Basal Culture Media

| Constituent | Concentration, mg/L | |
|---|---|---|
| | WTC[1] | $BM_G$[2] |
| BASAL SALTS | | |
| $NH_4NO_3$ | — | 206.3 |
| $KNO_3$ | varies[1] | 1170.0 |
| $CaCl_2.6H_2O$ | 200.0 | 220.0 |
| $Ca(NO_3)_2.4H_2O$ | varies[1] | — |
| $KH_2PO_4$ | 340.0 | 85.0 |
| $MgSO_4.7H_2O$ | 400.0 | 185.0 |
| $MnSO_4.H_2O$ | 20.8 | 8.45 |
| $ZnSO_4.7H_2O$ | 8.0 | 4.30 |
| $CuSO_4.5H_2O$ | 0.024 | 0.013 |
| $FeSO_4.7H_2O$ | 27.85 | 13.93 |
| $Na_2EDTA$ | 37.25 | 18.63 |
| $H_3BO_3$ | 5.0 | 3.10 |
| $NaMoO_4.2H_2O$ | 0.20 | 0.125 |
| $CoCl_2.6H_2O$ | 0.025 | 0.0125 |
| KI | 1.00 | 0.42 |
| ORGANIC ADDITIVES | | |
| myo-Inositol | varies[1] | 100.0 |
| Thiamine.HCl | 1.00 | 1.00 |
| Nicotinic acid | 0.50 | 0.50 |
| Pyridoxine.HCl | 0.50 | 0.50 |
| Glycine | 2.00 | 2.00 |
| L-Glutamine | varies | 450.0 |
| Casamino acids | 500.0 | — |
| Sugar as specified | varies | 20,000 |
| pH | 5.7 | 5.7 |

[1]Usage varies according to culturing stage and genotype.
[2]Modified Gupta and Durzan medium $BM_3$(1986). Medium $BM_G$ of U.S. Pat. No. 5,034,326.

TABLE 2

| | Stage I Initiation | Stage II Maintenance 1 | Stage III Maintenance 2 | Stage IV Singulation | Stage V Development | Stage VI Germination |
|---|---|---|---|---|---|---|
| Basal Medium | WTC | WTC | WTC | WTC | WTC | $BM_G$ |
| $KNO_3$ | 1250[1] | 1250–2500 | 1250 | 1050 | 1000–2500 | 1170 |
| $Ca(NO_3)_2 \cdot 4H_2O$ | — | — | — | 200 | — | — |
| myo-Inositol | 1000 | 5,000–10,000 | 5,000–10,000 | 100 | 100 | 100 |
| L-Glutamine | 450 | 450 | 1000 | 1000 | 750–1500 | — |
| Amino acid mixture[2] | — | — | — | — | 290 | — |
| Sugar | 15,000 | 30,000 | 30,000 | 20,000 | 20,000–60,000 | 20,000 |
| Supp. osmoticant | — | — | — | — | 30,000–300,000 | — |
| 2,4-D | 110 | 1.1 | 1.1 | — | — | — |
| $N^6$-Benzyladenine | 45 | 0.22 | 0.22 | — | — | — |
| Kinetin | 43 | 0.22 | 0.22 | — | — | — |
| Abscisic acid | — | — | — | 5–15 | 0–50 | — |
| Gibberellins $GA_n$ | — | — | — | 0–15 | 0.5–25 | — |
| Activated charcoal | 2500 | — | — | — | 0–2500 | 2500 |
| Agar | 5000 | 5000 | — | — | — | 8000[4] |
| Gelrite | — | — | — | — | 3000[3] | — |

[1] All units are in mg/L (or ppm).
[2] L-Proline - 100, L-Asparagine - 100, L-Arginine - 50, L-Alanine - 20, L-Serine - 20.
[3] Not used for liquid media.
[4] Tissue culture agar.
The pH of all media are adjusted to 5.7.

In Table 2 sucrose is the sugar used in Stage I and VI. In Stages II, III, IV, and V sucrose or maltose is used as shown in the specific examples. Glucose may also be used with maltose in stage V. Maltose has Generally proved to give superior results to sucrose in Stages II through V.

It will be seen by examining the media compositions that the features of the earlier inventions described in the patents incorporated by reference are advantageously used at present with Douglas-fir. A raised osmotic level following initiation is desirable for good quality advanced early stage embryo development. This level will differ somewhat between genotypes within each species as it does between species. Similarly, the level of abscisic acid present should be gradually reduced during the singulation stage and also during the cotyledonary embryo development period, if exogenous ABA is added in that stage. This may be done either by the inclusion of activated charcoal in the medium or by a stepwise reduction effected by multiple transfers to media of successively lower ABA concentration. The exogenous ABA level is preferably gradually reduced from that present at the beginning of the singulation stage so that little or none is available at the end of the development period.

The description that follows represents the best mode known at present for culturing Douglas-fir by somatic embryogenesis. A preferred explant for Douglas-fir is an immature zygotic embryo with the gametophyte still attached. Best results have been realized with embryos selected in the interval just prior to the development of an apical dome up to the time just before cotyledon primordia become visible. The cones are split longitudinally and seeds isolated from young ovuliferous scales. Seeds are sterilized by first being agitated in 10% Liqui-Nox laboratory cleaner (Alconox, Inc, New York, N.Y.) with a small additional amount of liquid surfactant for about 10 minutes. They are then rinsed in running tap water for 30 minutes. At this time they are transferred to a sterile hood and agitated in 20% $H_2O_2$ for 10 minutes. Following five rinses in sterile deionized water the seed coat is split and the female gametophyte removed. This is split on one side and the embryo teased out while still remaining attached to the gametophyte by the suspensor. An explant so prepared is placed on the Stage I solid initiation medium in a 50 mm petri dish. The explants are incubated in the dark from 4–8 weeks. Success in forming an embryonal-suspensor mass (ESM) containing early stage embryos varies from about 1–10% depending on a number of variable factors which presently are not well understood. Sucrose is the preferred sugar used in the initiation medium.

All stages of culture are carried out at temperatures which may vary between about 20°–25° C. Temperature is not generally critical and may, on occasion be varied so as to fall outside this range.

The embryonal-suspensor masses containing early stage embryos are transferred to a solid Stage II maintenance and multiplication medium containing greatly reduced plant growth hormones and a raised osmotic level. Again, culturing is carried out in the dark with subcultures made at no greater than about two week intervals. The clone can be maintained at this stage for long periods of time. In both the solid Stage II and the following Stage III liquid maintenance media maltose is substituted for the sucrose used in the initiation culture on an equal weight basis unless otherwise indicated in the following examples.

Early stage embryos from the Stage II multiplication step are then transferred to a liquid Stage III second maintenance medium having an osmotic level generally the same as that of the Stage II medium. An osmotic level of at least about 170 mM/kg will usually suffice for Douglas-fir although some genotypes may require levels as high as 240 mM/kg. Myo-inositol, which will normally be around 5000 mg/L, may need to be adjusted somewhat depending on the needs of the particular genotype in order to obtain optimum results. Culture is carried out in the dark and is periodically subcultured, usually weekly. Robust advanced early stage embryos estimated to have 100 or more cells will develop during this time, normally 5–6 weeks.

Following advanced early stage embryo development in Stage III, the cultures are transferred to a Stage IV liquid medium for the singulation step referred to earlier. Again, in this medium it has been found very beneficial to use maltose in preference to sucrose as the carbon and energy source. The singulation medium has a reduced osmotic level and is free of auxins and cytokinins. Abscisic acid is a newly added hormone in an initial amount in the range of about 5–15 mg/L, more usually about 5–10 mg/L. Cultures are again carried out in the dark. From two to four subcultures are made on a weekly basis. The level of exogenous abscisic acid will drop somewhat during each subculture. It is generally preferred that the level of abscisic acid at the beginning of a new subculture should not be significantly higher than the level used in the previous subculture. A preferred schedule is one week on a medium containing 10 mg/L ABA, a second week on a medium containing 5 mg/L ABA, and a third week on a medium also with 5 mg/L ABA. This gradual decrease in ABA level will continue through the development period.

After the final singulation treatment the embryos are rinsed with a fresh singulation medium in which ABA is reduced to 2.5 mg/L, before transfer to the cotyledonary development medium.

Following the singulation period the embryos are ready to complete their development to cotyledonary embryos on a Stage V medium. They are transferred to either a solid medium or supported on a pad or bridge of filter paper using a liquid medium. This will normally contain exogenous ABA which may be present up to about 50 mg/L. More typically, ABA will not generally exceed about 10 mg/L and most usually will not initially exceed 5 mg/L and may be considerably lower. In some cases it is not necessary to add any exogenous ABA to the development medium since a sufficient amount will be carried over with the residual singulation or rinse medium accompanying the embryos when the transfer is made from the last singulation stage. The development medium may also contain from 0.5–50 mg/L of a selected gibberellin. This is preferably $GA_{4/7}$. In cases where an adsorbent such as activated charcoal is not used in the development medium concentrations of GA and ABA will be significantly lower than the maximum levels just noted; e.g., by a full order of magnitude. The effect of osmotic level is discussed in detail in U.S. Pat. No. 5,036,007.

Following the development stage, the cotyledonary embryos are stratified by placing them in a 4° C. environment for about four weeks. They may then be placed on a Stage VI germination medium for production of plantlets. Alternatively, they may be placed in artificial seeds for sowing in soil or other medium.

EXAMPLE 2

Three genotypes of Douglas-fir embryos were taken from maintenance and singulated in a three step Stage IV treatment in which sucrose was present as the energy source. Embryos were then plated on two different Stage V development media. The first had 2.5% maltose as the energy source and the second had 2.5% maltose and 1% glucose. Each Stage V treatment had 72 plates or 24 replications per genotype. After 7 weeks on the development media the embryos were harvested for analysis. The 2.5% maltose medium represents the usual treatment and should be regarded as a control sample while the maltose plus glucose medium is an experimental medium. The mean results of the tests are given in Table 3.

TABLE 3

Treatment Means for Development Media Tests

| Parameter | 2.5% Maltose Control Means | 2.5% Maltose plus 1% Glucose Means | P Value |
|---|---|---|---|
| Embryo yield/plate | 123.08 | 126.9 | 0.5697 |
| Embryo root length, mm | 0.8 | 0.8 | 0.8167 |
| Embryo hypocotyl length, mm | 0.6 | 0.56 | 0.0479 |
| Embryo cotyledon length, mm | 0.39 | 0.41 | 0.2232 |
| Embryo total length, mm | 1.79 | 1.78 | 0.7821 |
| Dry weight/embryo, mg | 0.23 | 0.28 | 0.0001 |
| Stachyose/embryo (nmoles) | 0.4 | 0.7 | 0.0003 |
| Stachyose/mg dry wt. (nmoles) | 2.02 | 2.71 | 0.0184 |
| Raffinose/embryo (nmoles) | 1.65 | 2.8 | 0.0001 |
| Raffinose/mg dry wt. (nmoles) | 8.27 | 10.94 | 0.0105 |
| Sucrose/embryo (nmoles) | 64.3 | 89.57 | 0.0001 |
| Sucrose/mg dry wt. (nmoles) | 319.44 | 356.95 | 0.1204 |
| Melibiose/embryo (mnoles) | 0.75 | 0.85 | 0.1772 |
| Melibiose/mg dry wt. (nmoles) | 3.28 | 3.14 | 0.6533 |
| Fructose/embryo (nmoless) | 9.08 | 9.39 | 0.7127 |
| Fructose/mg dry wt. (nmoles) | 39.73 | 33.6 | 0.0672 |
| Glucose/embryo (nmoles) | 9.08 | 7.22 | 0.1042 |
| Glucose/mg dry wt. (nmoles) | 38.65 | 26.17 | 0.0045 |
| Galactose/embryo (nmoles) | 0.51 | 0.61 | 0.0967 |
| Galactose/mg dry wt. (nmoles) | 2.34 | 2.32 | 0.9353 |
| Germinant browning, % | 16.8 | 11.9 | 0.0481 |
| Germinant root length, mm | 5.14 | 5.02 | 0.5335 |
| Root normalcy, % | 22.9 | 17.5 | 0.0161 |
| White root, % | 5.7 | 4.9 | 0.396 |
| Epicotyl initiation, % | 68.7 | 78 | 0.0001 |

It can be seen from these results that even though the embryos from the two treatments were visually and by measurement morphologically almost identical, there were major biochemical differences which later manifested themselves in superior germinants. There was a significant effect seen for dry weight, sucrose, and the higher oligosaccharides raffinose and stachyose. These differences represented relatively large changes in the biochemistry relative to the control treatment. The oligosaccharide response was more pronounced for two of the three genotypes investigated. It has been noted that some genotypes fail completely to develop raffinose and stachyose at this stage of development on the control medium.

The differences between the control treatment and experimental medium are further seen when embryos were germinated on Stage VI medium. Leaf/cotyledon, epicotyl initiation percentage, and epicotyl leaf percentage were statistically improved by the experimental treatment although there was a small decrease in root normalcy. Browning also was significantly reduced using the experimental medium. Other experiments have shown that there is a decrease in root performance that appears to correlate with improved epicotyl performance. This may simply be the result of competition for resources by a more vigorous shoot.

Thus, the effect of adding glucose to the development medium was statistically significant. The value of using our method of determining sucrose series oligosaccharides to screen biochemical differences between morphologically similar somatic embryos has been clearly shown. The value of the method for screening the efficiency of various culture media formulations is also clearly evident.

It might be noted that the selection of seven weeks for removal of the embryos from the development medium was somewhat arbitrary and was largely based on morphological appearance. It is difficult to know without further work whether biochemical maturation was still occurring in either or both of the control and experimental samples.

It is interesting that the one genotype studied that responded most from the standpoint of oligosaccharide increase previously had the poorest transplantability performance due to poor epicotyl development.

EXAMPLE 3

Figure 2:
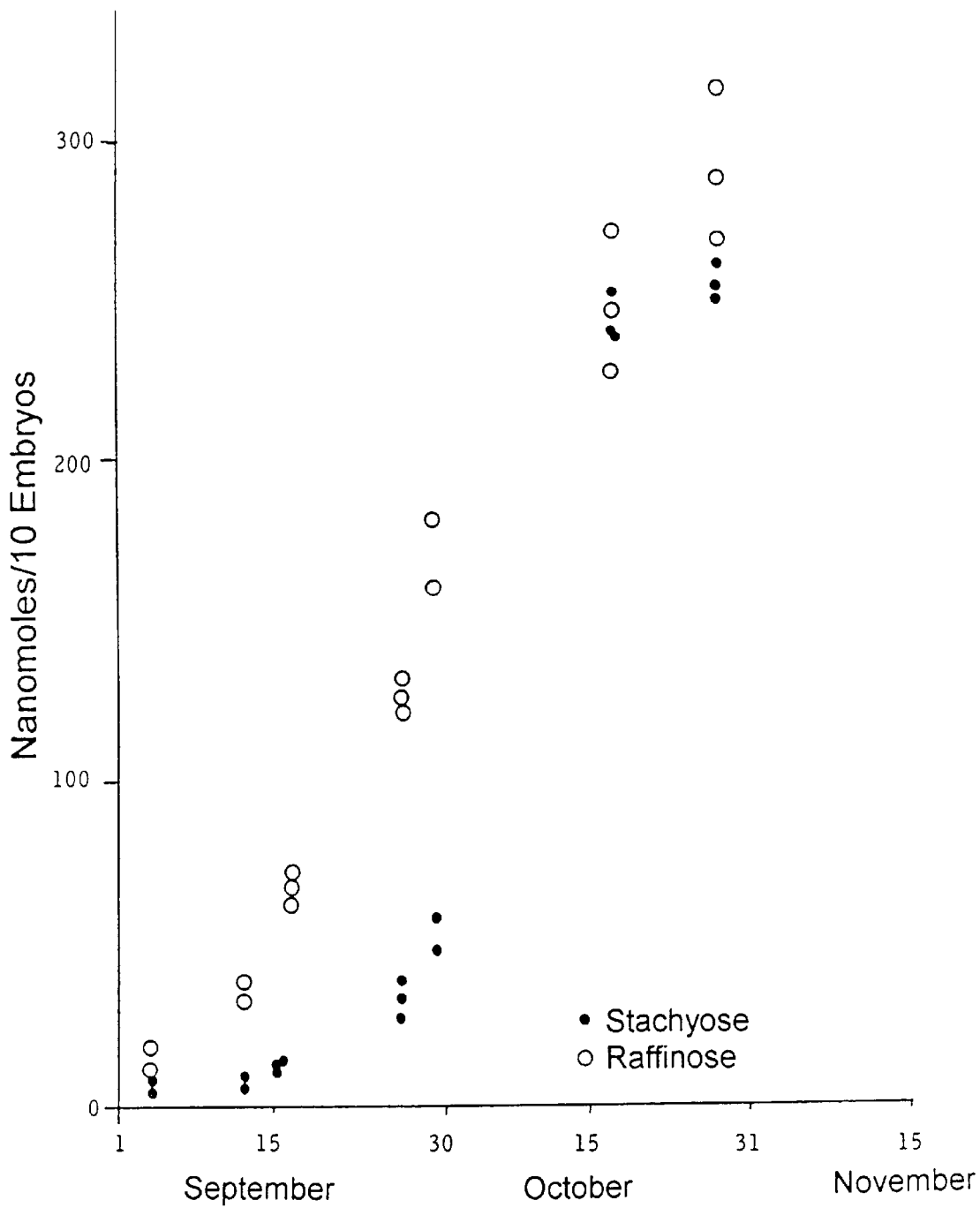
FIG. 2 is a graph showing development of complex sugars in loblolly pine embryos.

FIG. 2 shows data for the development of the oligosaccharides raffinose and stachyose for loblolly pine embryos. Cones were taken from a single tree in an Arkansas nursery and embryos taken periodically during September and October were analyzed for these two sugars. As with Douglas-fir, they show a very low content prior to morphological maturity. However, the complex sugars rise about linearly to high values at embryo biochemical maturity.

LOBLOLLY PINE CULTURE

The following schedule of treatments has been very successfully used for the growth of plantlets by somatic embryogenesis of loblolly pine (*Pinus taeda*). Explants were the female gametophytes containing the zygotic embryos which had been removed from seeds 4 to 5 weeks after fertilization. The seed coat was removed but the embryo was not further dissected out of the surrounding gametophyte other than to excise the nucellar end. Seeds were obtained from cones supplied by a Weyerhaeuser Company seed orchard located at Washington, North Carolina. The cones were stored at 4° C. until used. Immediately before removal of the immature embryos the seeds were sterilized using a modified method of Gupta and Durzan (1985). Briefly, this involves an initial washing and detergent treatment followed by a 10 minute sterilization in 15% $H_2O_2$. The additional $HgCl_2$ treatment used by Gupta and Durzan was not found to be necessary to ensure sterility. The explants were thoroughly washed with sterile distilled water after each treatment.

Tables 4 and 5 give media compositions for loblolly pine embryogenesis.

TABLE 4

*Pinus Taeda* Basal Medium (Modified ½ P6 Basal Salts*)

| Constituent | Concentration mg/L |
|---|---|
| $NH_4NO_3$ | 150.0 |
| $KNO_3$ | 909.9 |
| $KH_2PO_4$ | 136.1 |
| $Ca(NO_3)_2.4H_2O$ | 236.2 |
| $CaCl_2.4H_2O$ | 50.0 |
| $MgSO_4.7H_2O$ | 246.5 |
| $Mg(NO_3)_2.6H_2O$ | 256.5 |
| $MgCl_2.6H_2O$ | 50.0 |
| KI | 4.15 |
| $H_3BO_3$ | 15.5 |
| $MnSO_4.H_2O$ | 10.5 |
| $ZnSO_4.7H_2O$ | 14.4 |
| $NaMoO_4.2H_2O$ | 0.125 |
| $CuSO_4.5H_2O$ | 0.125 |
| $CoCl_2.6H_2O$ | 0.125 |
| $FeSO_4.7H_2O$ | 13.9 |
| $Na_2EDTA$ | 18.65 |
| Sucrose | 30,000. |
| myo-Inositol | 100 |
| Casamino acids | 500 |
| L-Glutamine | 1000 |
| Thiamine.HCl | 1.00 |
| Pyridoxine.HCl | 0.50 |
| Nicotinic acid | 0.50 |
| Glycine | 2.00 |
| Agar+ | 6,000 |
| pH adjusted to 5.7 | |

*According to Teasdale, Dawson, and Woolhouse (1986) as modified
+Used if a solid medium is desired

Table 5

Composition of Media for Different Stage Treatments $BM_1$—Induction Medium
  BM+2,4-D (15 μM)+KIN (2 μM)+BAP (2 μM)

$BM_2$—Maintenance and Multiplication Medium
  BM+2,4-D (5 μM)+KIN (0.5 μM)+BAP (0.5 μM)+ 4900 mg/L additional myo-inositol. Maltose is substituted for sucrose on an equal weight basis. Agar is added when a solid medium is desired.

$BM_3$—Cotyledonary Embryo Development Medium
  BM+50 mg/L abscisic acid+18% PEG-4000 & 8000 MIXTURE +2–6% maltose+900 mg/L additional myo-inositol+1000 mg/L glutamine+0.125% activated charcoal. No gellant. The following amino acid mixture is added: L-proline—100 mg/L, L-asparagine—100 mg/L, L-arginine—50 mg/L, L-alanine 20 mg/L, and L-serine—20 mg/L.

$BM_4$—Germination Medium
  BM modified by reducing sucrose to 20,000 mg/L, myo-inositol to 100.0 mg/L, glutamine and casamino acids to 0.0 mg/L+0.6% agar and 0.25% activated charcoal.

Stage I—Induction Sterile gametophytes with intact embryos were placed on a solid BM, culture medium and held in an environment at 22°–25° C. with a 24 hour dark photoperiod for a time of 3–5 weeks. The length of time depended on the particular genotype being cultured. At the end of this time a white mucilagenous mass had formed in association with the original explants. This appears to be identical with that described by Gupta and Durzan (1987). Microscopic examination revealed numerous early stage embryos associated with the mass. These are generally characterized as having a long thin-walled suspensor associated with a small head with dense cytoplasm and large nuclei. Typical early stage embryos are illustrated in FIG. 1.

Osmolality of the induction medium may in some instances be as high as 170 mM/kg. Normally it will be about 160 mM/kg or even lower. The osmolality of the medium described above was 150 mM/kg.

Stage II—Maintenance and Multiplication Early stage embryos removed from the masses generated in the induction stage were first placed on a $BM_2$ gelled maintanance and multiplication medium. This differs from the induction medium in that the growth hormones (both auxins and cytokinins) were reduced by at least a full order of magnitude. Osmolality of this medium will typically be raised from that of the induction medium to about 180 mM/kg or higher by increasing the concentration of myo-inositol to 0.5% w/v. The temperature and photoperiod were again 22°–25° C. with 24 hours in the dark. Embryos were cultured 12–14 days on the $BM_2$ solid medium before transferring to a liquid medium for further subculturing. This liquid medium was of similar composition but lacked the gellant. The embryos at the end of the solid maintenance stage were similar in appearance to those from Stage I. After 5 to 6 weekly subcultures on the liquid maintenance medium advanced early stage embryos had formed. These are characterized by smooth embryonal heads estimated to have over 100 individual cells with multiple suspensors, as exemplified in FIG. 2.

Osmotic potential of the maintenance media should typically fall within the range of about 180–400 mM/kg for *Pinus taeda*. Most typically they should be in the neighborhood of about 1.5 times higher than that of the induction or multipliction media. As was noted earlier, the requirements for elevation of osmotic potential at this stage will vary for different species and may vary somewhat even for differing genotypes within a given species.

Stage III—Embryo Development The advanced early stage embryos from Stage II culture were transferred to a filter paper support placed on a pad saturated with liquid development medium. This medium either lacks growth hormones entirely or has them present only at very low levels and has the same lower level of osmoticants as Stages I and II. However, here abscisic acid (5-(1-hydroxy-2,6,6-trimethyl-4-oxo-2-cyclohexen-1-yl)-3-methyl-2,4-pentadienoic acid) appears to be a necessary material for further development. As was noted earlier the further inclusion of an adsorbent material in this medium is highly advantageous. The adsorbent may be chosen from a number of chemical materials having extremely high surface area and/or controlled pore size such as activated charcoal, soluble and insoluble forms of poly(vinyl pyrrolidone), activated alumina, silica gel, molecular sieves, etc. The adsorbent will normally be present in a concentration of about 0.1–5 g/L, more generally about 0.25–2.5 g/L.

The osmotic potential of this medium may be raised substantially over that of the maintenance medium. It has been found advantageous to have an osmolality as high as 350 mM/kg or even higher. As before, development is preferably carried out in complete darkness at a temperature of 22°–25° C. Development time was 12 weeks after which elongated cotyledonary embryos 2–3 mm long were present.

Stage IV—Drying The embryos still on their filter paper support are lifted from the pad and placed in a closed container over a saturated solution of $K_2SO_4$, at a relative humidity of 97%, for a period of three weeks.

Stage V—Germination The dried cotyledonary embryos from Stage IV were rehydrated by placing them, while still on the filter paper support, for about 24 hours on a pad saturated with liquid germination medium. The embryos were then placed individually on solid $BM_4$ medium for germination. This is a basal medium lacking growth hormones which has been modified by reducing sucrose, myo-inositol and organic nitrogen. After about 6–8 weeks under environmental conditions of 23°–25° C. and a 16 hour light—8 hour dark photoperiod the resulting plantlets were approximately 20 mm in length and had a well developed radicle and hypocotyl and green cotyledonary structure and epicotyl. Alternatively, the cotyledonary embryos may be made into artificial seeds.

Because of the reduced carbohydrate concentration, the osmotic potential of the germination medium is further reduced below that of the development medium. It will normally be below about 150 mM/kg and was, in the present example, about 100 mM/kg.

Stage VI—Conversion Plantlets from Stage V were removed from the germination medium and planted in a soil comprising equal parts of peat and fine perlite. Rooting percentage was excellent and the resulting plants showed good growth and vigor.

Two genotypes of loblolly pine were cultured as described above. The embryos were removed from the development medium still on their filter paper supports and placed for drying over saturated $K_2SO_4$ solution for three weeks. Duplicate samples of each genotype were taken before and after the drying period. Those used for sugar analysis were rehydrated for only one hour and then immediately frozen in liquid nitrogen. Sugars were determined by the high pressure liquid chromatography procedure outlined earlier. Three replicate determinations were run on each sample taken before drying and two replicate determinations on the samples after drying. Mean values of sugars for each of the treatments are given in Table 6 which follows.

TABLE 6

Sugars in Pine Somatic Embryos before and After Drying

|  | Genotype 5 | | Genotype 7 | |
| --- | --- | --- | --- | --- |
|  | Before Drying | After Drying | Before Drying | After Drying |
| Glucose/embryo, nm[1] | 1.26 | 2.79 | 1.27 | 2.46 |
| Glucose/mg dry wt., nm | 6.57 | 14.48 | 7.18 | 6.3 |
| Fructose/embryo, nm | 0.75 | 4.72 | 1.04 | 2.4 |
| Fructose/mg dry wt., nm | 3.87 | 20.47 | 5.85 | 6.14 |
| Sucrose/embryo, nm | 5.81 | 34.68 | 10.86 | 52.59 |
| Sucrose/mg dry wt, nm | 30.13 | 179.29 | 61.55 | 131.41 |
| Raffinose/embryo, nm | 0.16 | 0.98 | 0.2 | 3.19 |
| Raffinose/mg dry wt., nm | 0.8 | 4.72 | 1.14 | 7.78 |
| Stachyose/embryo, nm | <1 | 0.2 | <1 | 0.57 |
| Stachyose/mg dry wt., nm | <1 | 0.98 | <1 | 1.39 |

[1]nanomoles

For both genotypes, raffinose and stachyose were at very low levels before drying and rose significantly during the drying treatment. Somewhat surprisingly, sucrose rose by a factor of almost 6 during drying for Genotype 5 but by only a factor of 2.1 for Genotype 7. There was a major difference between genotypes in the simple sugars. Glucose and fructose rose sharply during drying in Genotype 5 but were little changed in Genotype 7. This is contrary to the behavior seen in conifer zygotic enbryos. Raffinose and stachyose both increased to a greater extent in Genotype 7 than in Genotype 5.

It appears that the higher absolute levels of raffinose and stachyose affect germinability positively since embryos of Genotype 7 are known to germinate more readily than those of Genotype 5. Germinability of both genotypes before drying was essentially nil. This reinforces the similar conclusions based on the data for Douglas-fir given in Table 3.

EXAMPLE 4

Somatic embryos of Douglas-fir (*Pseudotsuga menziesii* (Mirb.) Franco) were grown; e.g., as described in U.S. Pat. No. 5,036,007 to Gupta et al. or U.S. Pat. No. 5,563,061 to Gupta, using the media and protocol described in Tables 1 and 2 herein. Morphologically mature embryos were removed from the development medium and incubated for four days with different amounts of water vapor or free water. Humidities were 92.5% or 98%. In the latter case 0, 1, or 2 mL of free water was present.

The embryos were extracted and dehydrin was determined using an immnuno-blot of an SDS-polyacrylamide gel. Briefly, protein content in extracts was first measured by Bio-Rad protein assay. Extracts of total heat soluble proteins were then dissolved and heated at 90° C. in SDS-sample buffer. Proteins were electrophoresed through 6–18% SDS-polyacrylamide gels. After electrophoresis, proteins were electroblotted to nitrocellulose. Blots were first stained for 10 minutes in 0.5% w/v Ponceau S in 1% v/v glacial acetic acid to determine the positions of reference molecular weight markers, and then completely destained in water. The remainder of the blotting procedure was done similar to that described in Copeland (1994) and as essentially described in the technical manual supplied with the horseradish peroxidase detection kit (Bio-Rad Immun-Blo™ Assay Kit, available from Bio-Rad Laboratories, Hercules, California). Incubation times, antibody dilutions and blocking agent were optimized empirically and resulted in the following modifications. Blots were blocked in gelatin (3% w/v) for 1 hour and probed for 2 hours in a 1:1000 dilution of primary antibody which was a C-terminal consensus sequence from pea dehydrin (Stress-gen Biotech) in 1% gelatin. Blots were then incubated in a 1:100 dilution of secondary antibody (peroxidase labeled goat anti-rabbit lgG) for 1 hour in 1% gelatin. Color development was as described by Bio-Rad.

Figure 3:
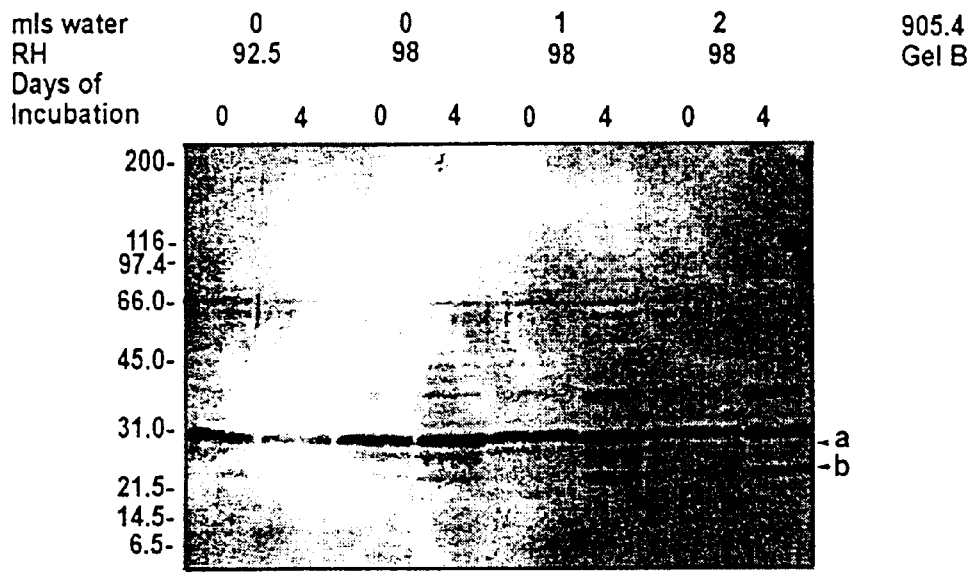
FIG. 3 is an immuno-blot showing the dehydrin-like proteins formed in somatic embryos on exposure to high humidities or free water

Gel electrophoresis results in proteins being separated on the gel according to their relative molecular weights (Mr) with the smallest protein being towards the bottom and the highest molecular weight at the bottom (FIG. 3). The position of migration of reference proteins of known molecular weight is indicated in the left hand margin. Two forms of dehydrin-like proteins are observable following the inmmunoblotting procedure, One form (a) is of Mr=29,000 and the other (b) is about Mr=23,000. Experience has shown that the precise molecular weights of these forms will be somewhat species dependent.

Figure 4:
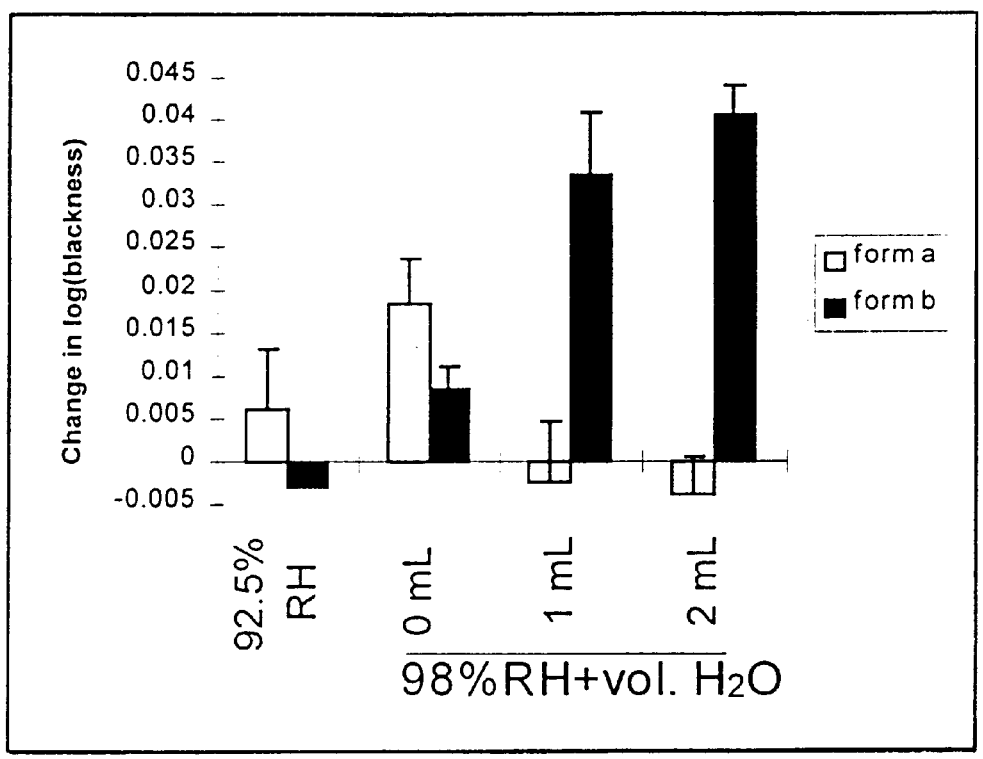
FIG. 4 is a bar graph showing compiled results of six gels analyzed by densitometry to show relative amounts of two dehydrin forms.

FIG. 4 is a graph showing the compiled results of six such gels where the gels have been analyzed by densitometry. The level of protein is proportional to the log of the blackness. Each bar represents the mean change ($\pm$s.e., n=6) in log blackness resulting from the specified treatment. Incubation at 98% R.H. without free water results in a significant ($\alpha$=0.05, paired sample t-test) increase in the level of both forms (a) and (b). Incubation at 98% R.H. with either 1 or 2 mL free water results in a significant increase only in lower molecular weight form (b).

EXAMPLE 5

Figure 5:
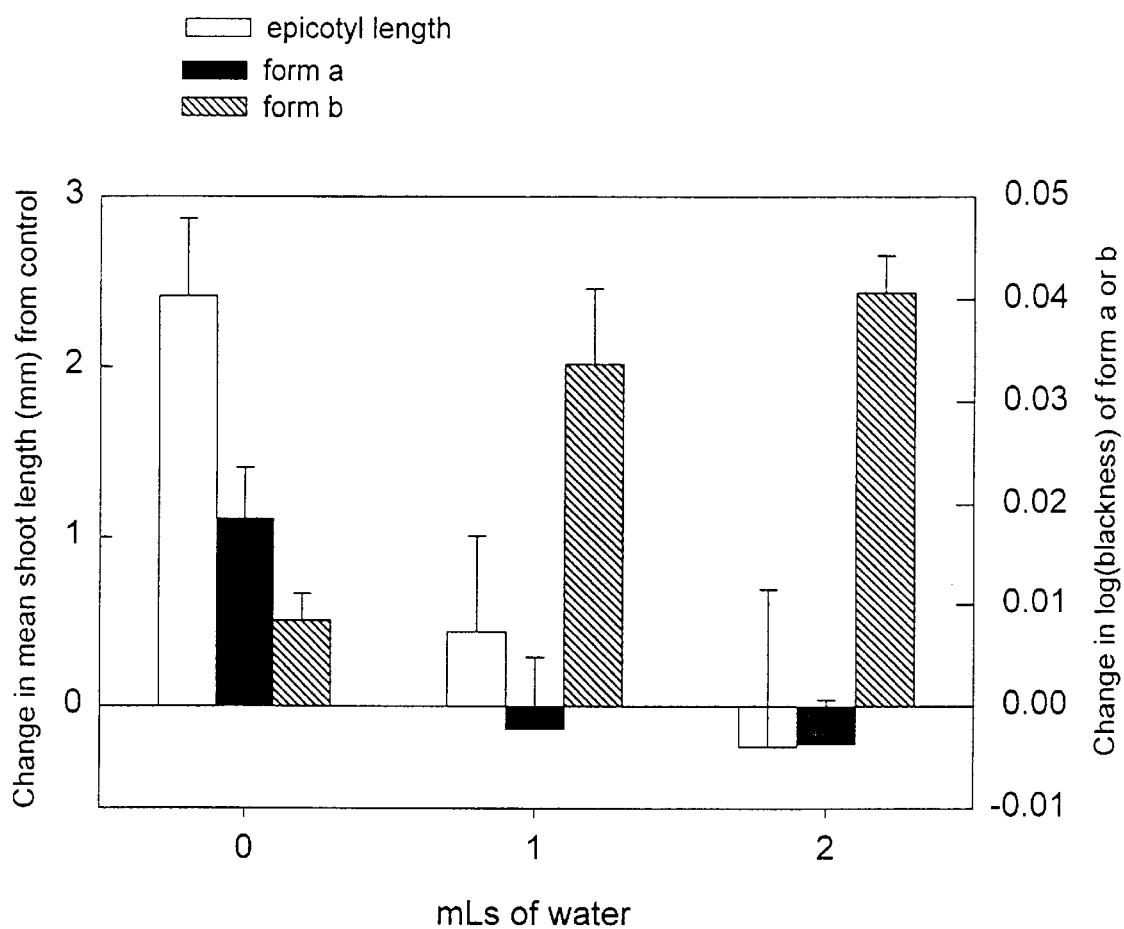
FIG. 5 is a bar graph showing that a significant increase in somatic embryo germinant stem length correlates with an increase in one form of dehydrin proteins in the embryos.

Germination is generally considered to have occurred upon a visible increase in axis length of the embryo. FIG. 5 is a bar graph showing that a significant ($\alpha$=0.05) increase in dehydrin-like protein, form (a), but not form (b) is associated with a significant increase ($\alpha$=0.05) in epicotyl stem length when the embryos from the treatments in Example 1 are placed in an environment conducive to germination. All of the three treatments at 98% R.H. (0, 1, or 2 mL of free water) caused a significant increase in dehydrin form (b). This increase was markedly lower for the embryos incubated without free water. Only incubation at 98% R.H. without free water caused a significant increase in epicotyl stem length. This sample had an associated simultaneous significant increase in the level of dehydrin form (a). These data indicate that formation of dehydrin form (a), which occurs upon incubation of somatic embryos at high relative humidity in the absence of free water, is associated with an increase in quality of the embryos.

Figure 6:
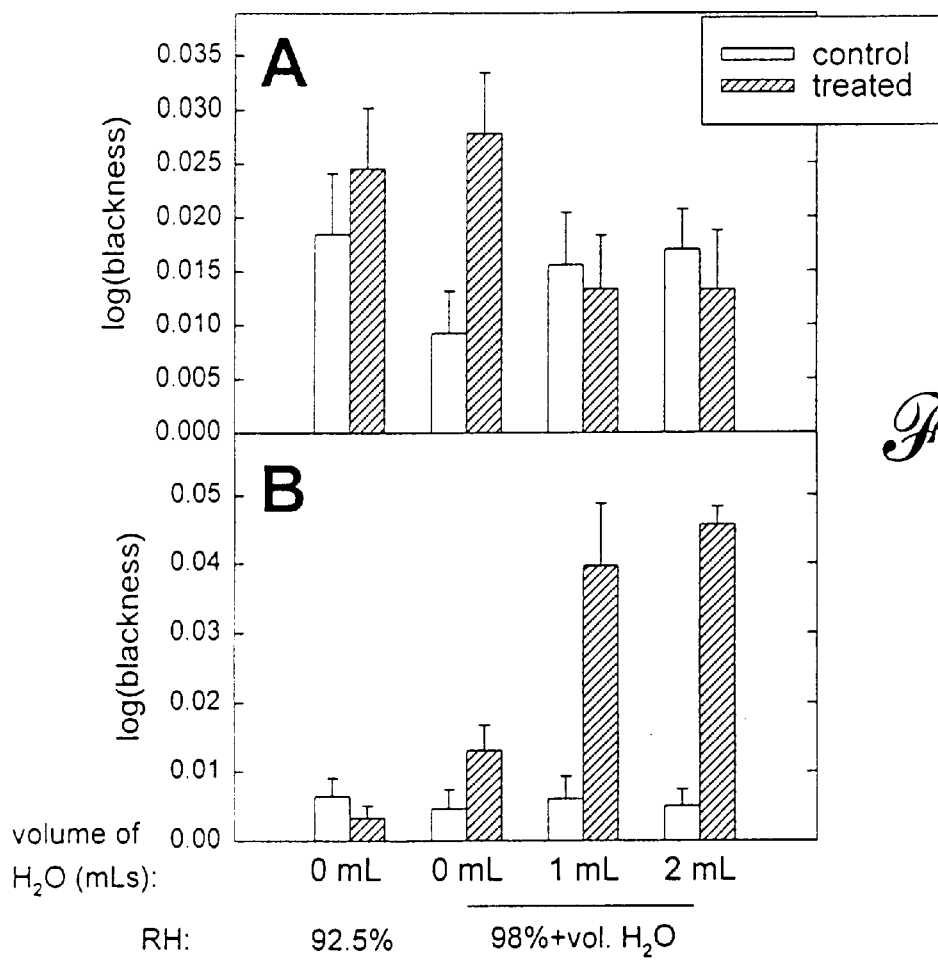
FIG. 6 is a pair of bar graphs showing that an increase in one form of dehydrin proteins, but not the other, correlates well with an increase in epicotyl tuft length.
Figure 7:
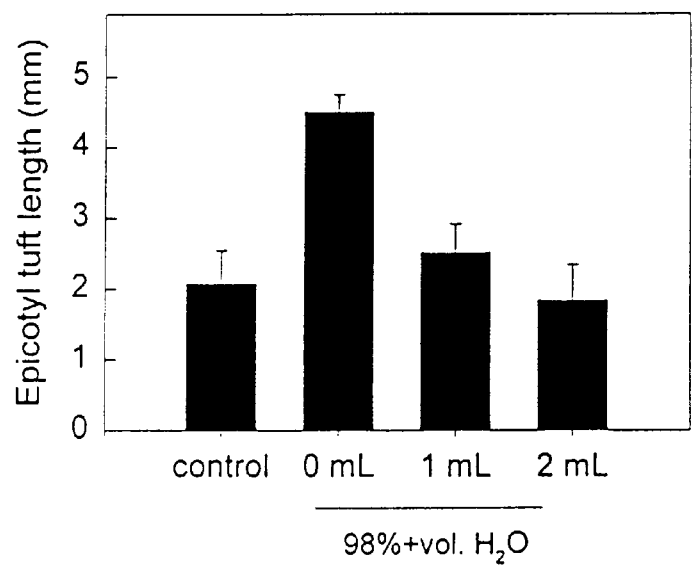
FIG. 7 is a bar graph showing increase in epicotyl tuft length for germinated embryos treated at 98% R.H. with and without free water.
Figure 8:
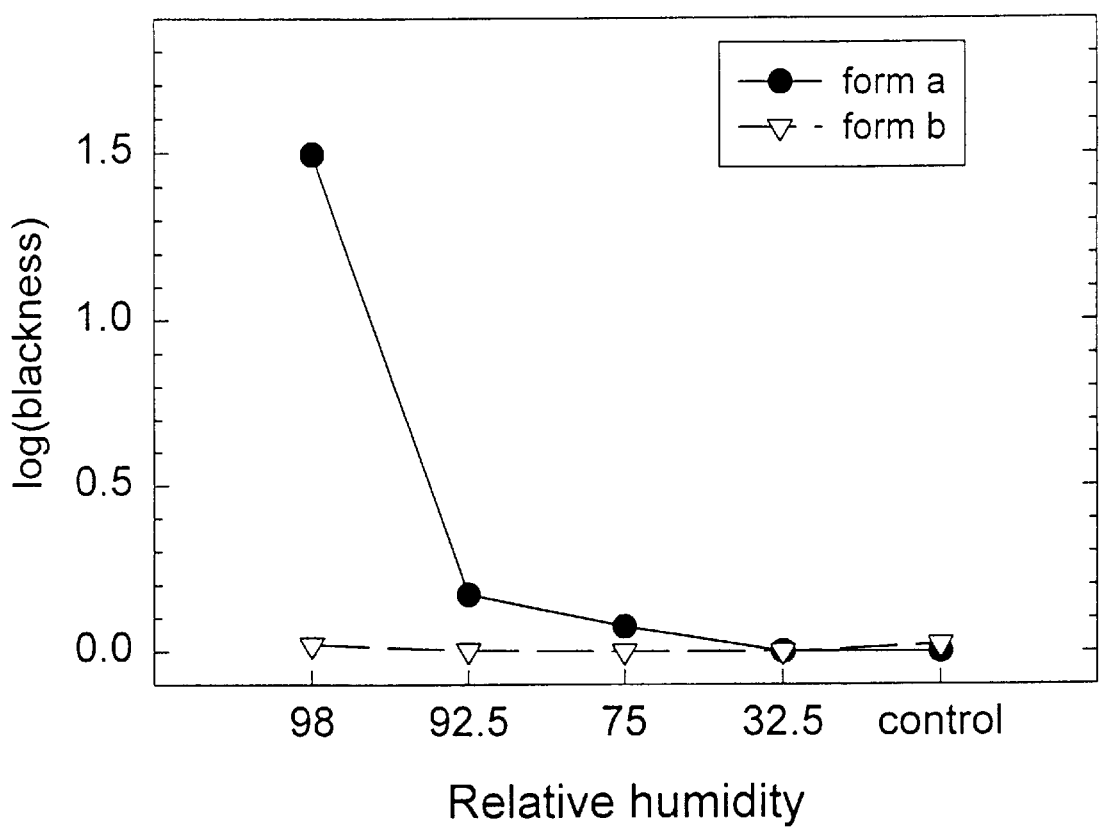
FIG. 8 is a graph showing the formation of two dehydrin forms in somatic embryos treated over a range of relative humidities.

Similar results are seen when epicotyl tuft length is examined. Epicotyl tuft length is considered to be the sum of the lengths of the epicotyl stem and true leaves. FIG. 6 is a pair of bar graphs showing that a significant ($\alpha$=0.05) increase in dehydrin form (a) (Graph A) but not dehydrin form (b) (Graph B) is associated with a significant ($\alpha$=0.05) increase in epicotyl tuft length. Embryos were incubated at 92.5% R.H. and at 98% R.H. Those embryos at the higher R.H. had 0, 1, or 2 mL of free water present. FIG. 7 is a bar graph showing epicotyl tuft length for the germinated embryos treated at 98% R.H. Control embryos in all cases were taken directly from development medium without incubation.

It is greatly preferred that the incubation to induce dehydrin should take place at a relative humidity of 95% or greater.

The increase in dehydrin form (a) is seen to correlate closely with the increase in epicotyl tuft length of the germinated embryos.

EXAMPLE 6

It appears that the formation of dehydrin form (a) with incubation at higher relative humidities is correlated with an increase in growth rate. FIG. 6 is based on densitometry of immuno-blot gels and shows the level of both forms of dehydrin in Douglas-fir somatic embryos after incubation for ten days at various R.H. levels. Dehydrin form (b) remained at extremely low levels throughout while form (a) was at relatively high levels only when the embryos were incubated at 98% R.H.

Figure 9:
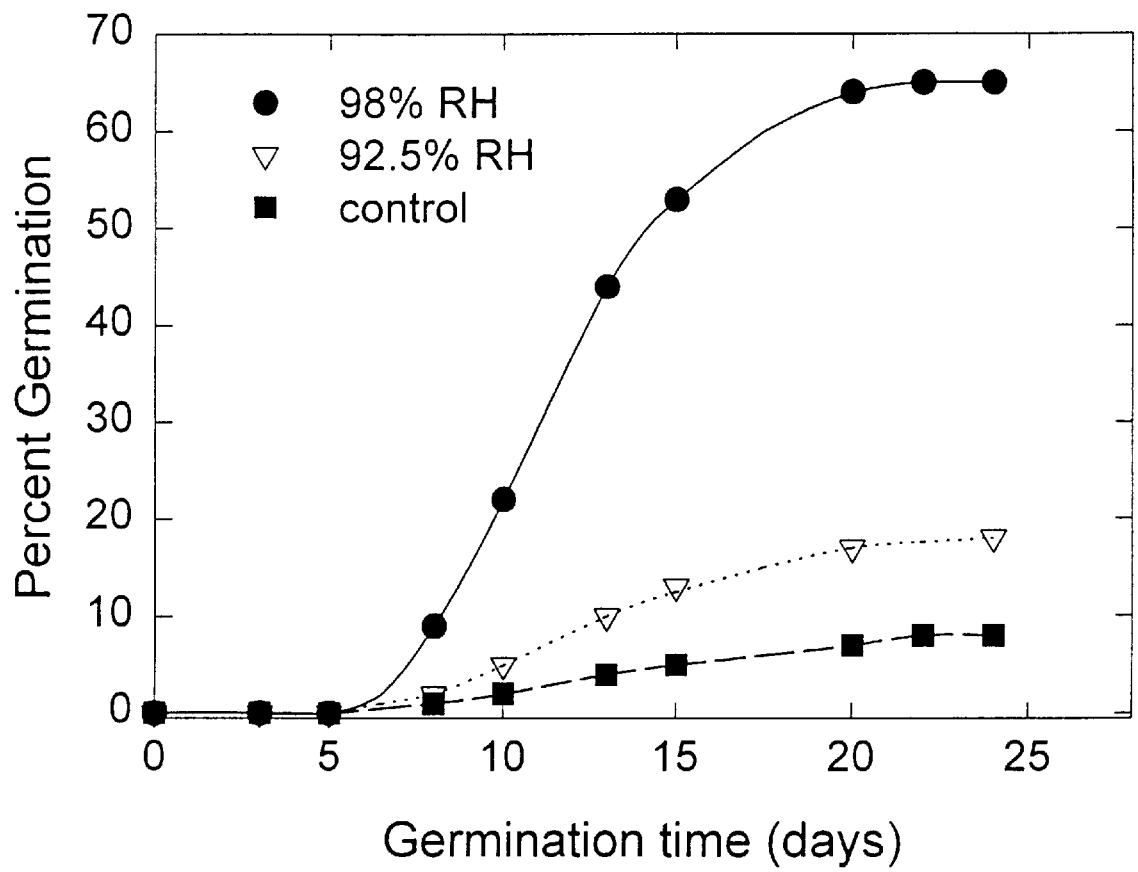
FIG. 9 is a graph indicating germination percentages of somatic embryos treated at various relative humidities.

The percentage germination as a function of time for embryos treated at 92.5% and 98% R.H. is seen in FIG. 9. A germinant is considered to be an embryo showing a root length greater than 2 mm. The control sample consisted of embryos removed directly from development medium without further conditioning. Over the 25 days of the test the superior germination of the Douglas-fir embryos conditioned at 98% R.H. is immediately apparent.

EXAMPLE 7

Figure 10:
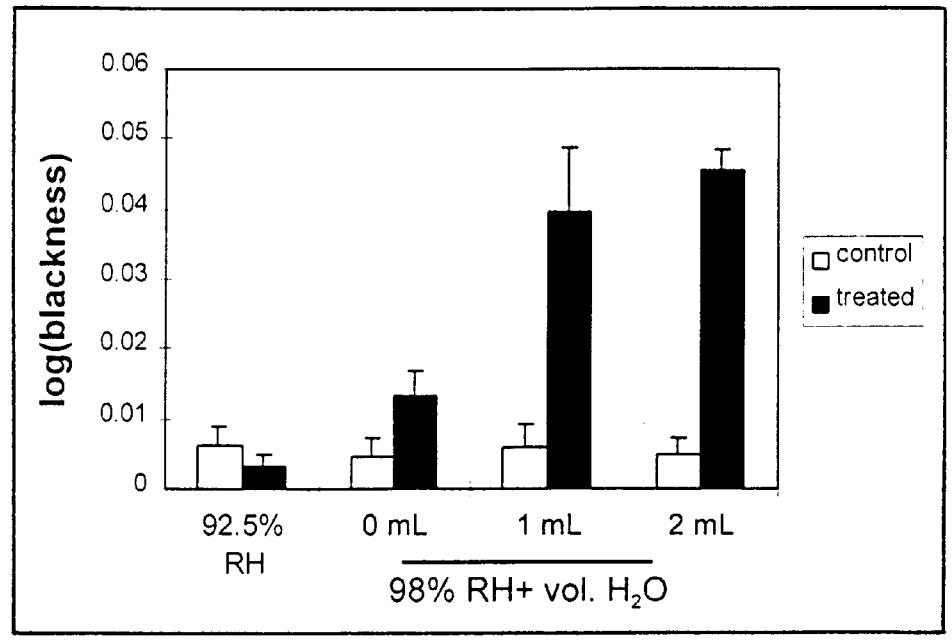
FIG. 10 is a bar graph showing the increase in a lower molecular weight form of dehydrin following incubation at various relative humidity conditions.

This example shows that the formation of dehydrin form (b) in somatic embryos is indicative of the onset of germination. Further, it indicates that if this occurs before the embryos have been placed in an appropriate supportive environment, the effects can be detrimental, as was also seen in Example 2. FIG. 10 shows the increase in dehydrin form (b) after treatment at four days at 92.5% R.H. and 98% R.H. At the higher humidity the treatments had 0, 1, or 2 mL of free water present. Bar graph values were determined by densitometry of immuno-blots. Control samples were taken directly from development medium without incubation.

Figure 11:
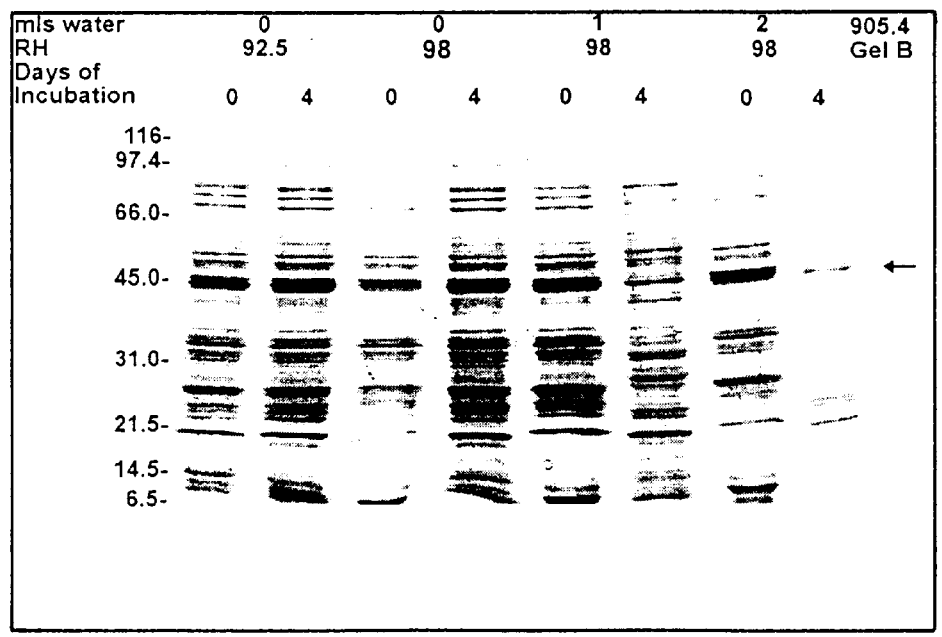
FIG. 11 represents a series of gels showing disappearance of one storage protein under unfavorable conditions of incubation.

FIG. 11 portrays a gel showing extracts of the above treated embryos at the beginning of the treatment and after four days. A strong legumin protein band is seen at a molecular weight of 45 kDa. This protein is generally considered to be one of the storage reserves in the embryo. In particular, as seen in the embryos treated at 98% R.H. with liquid water present, this 45 kDa band decreases after four days treatment. This is indicative that the protein is being prematurely catabolized and will not be available to the embryo after germination. However, there is no indication of premature disappearance after four days of the 45 kDa band in the embryos treated at 98% R.H. without liquid water.

It is evident from the above data that the use of the embryo development model using sugar and dehydrin group protein analysis is a valuable new tool for the scientists researching conifer embryogenesis. It can be of major assistance in determining embryo biochemical maturity and readiness to germinate as well as guiding the formulation of more effective culture media. The net result is somatic embryos that may be more readily converted into normal and vigorous plants.

Thus our invention comprises conifer somatic embryos having a significant presence of sucrose series oligosaccharides. It further comprises conifer somatic embryos having elevated amounts of dehydrin group proteins. In addition it comprises determination of sucrose series oligosaccharides and dehydrin group proteins as a method of evaluating biochemical maturity of the embryos.

Our invention also comprises treatment of morphologically mature somatic embryos at high relative humidity for a sufficient time for adequate levels of dehydrins to develop. It additionally comprises examination of dehydrin content of somatic embryos as a biochemical marker or indicator of maturity and of dehydrin decomposition products as indicators of the onset of germination.

It will be evident to those skilled in the art that many variations can be made in our invention that have not been described in the examples. It is the intent of the inventors that these variations should be considered within the scope of the invention if they are encompassed within the appended claims.

Bibliography:

Attree, S. M. and L. C. Fowke 1995 Desiccated conifer somatic embryos. U.S. Pat. No. 5,464,769.

Becwar, M. R., E. E. Chesick, L. W. Handley, III, and M. R. Rutter 1995 Method for regeneration of coniferous plants by somatic embryogenesis. U.S. Pat. No. 5,413,930. 1996 Method for regeneration of coniferous plants by somatic embryogenesis. U. S. Pat. No. 5,506,136.

Bernal-Lugo, I. and A. C. Leopold 1992 Changes in soluble carbohydrates during seed storage. *Plant Physiology* 98: 1207–1210.

Black, M, F. Corbineau, M. Grzesik, P. Guy, and D. Come 1996 Carbohydrate metabolism in the developing and maturing wheat embryo in relation to its desiccation tolerance. *Journal of Experimental Botany* 47 (295): 161–169.

Blackman, S. A., R. L. Obendorf, and A. C. Leopold 1992 Maturation proteins and sugars in desiccation tolerance of developing soybean seeds. *Plant Physiology* 100: 225–230. Ching, T. M. 1966 Compositional changes of Douglas-fir seeds during germination *Plant Physiology* 11: 1313–1319.

Close, T. J., R. D. Fenton, and F. Moonan 1993 A view of plant dehdrins using antibodies specific to their carboxy terminal petide. *Plant Molecular Biology* 23: 279–286.

Copland, R. A. 1994 Methods for protein analysis. Chapman and Hall, New York

Dure III, L., M. Crouch, J. Harada, T. D. Ho, J. Mundy, R. Quatrano, T. Thomas, and Z. R. Sung 1989 Common amino acid sequence domains among the LEA proteins of higher plants. *Plant Molecular Biology* 12: 475–486.

Durzan, D. J. and V. Chalupa 1968 Free sugars, amino acids and soluble proteins in the embryo and female gametophyte of jack pine as related to climate at the seed source. *Canadian Journal of Botany* 46: 417–428.

Frias, J., C. Vidal-Valverde, H. Kozlowska, R. Gorecki, J. Honke, and C L. Hedley 1996 Evolution of soluble carbohydrates during the development of pea, faba bean and lupin seeds. *Z. Lebensm. Utter. Forsh.* 203: 27–32.

Galau, G. A., K. S. Jakobsen, and D. W. Hughes. 1991 The control of late dicot embryogenesis and early germination. *Physiologia Plantarum* 81: 280–288.

Gupta, P. K. 1996 Method for reproducing conifers by somatic embryogenesis using a maltose enriched maintenance medium. U.S. Pat. No. 5,563,061 (1996).

Gupta, P. K. and G. S. Pullman 1990 Method for reproducing coniferous plants by somatic embryogenesis. U.S. Pat. No. 4,957,866. 1991 Method for reproducing coniferous plants by somatic embryogenesis using abscisic acid and osmotic potential variation. U. S. Pat. No. 5,036,007.

Han, B, and A. R. Kermode. Dehydrin-like proteins in castor bean seeds and seedlings are differentially produced in response to ABA and water-deficit-related stresses. *Journal of Experimental Botany* 47 (300): 933–939 (1996).

Han, B., D. W. Hughes, G. A. Galau, J. D. Bewley, and A. R. Kermode 1997 Changes in late-embryogenesis-abundant (LEA) messenger RNAs and dehydrins during maturation and premature drying of *Ricinus communis L.* seeds. *Planta* 201 (1): 27–35.

Handley, L. W., D. M. Pharr and R. F. McFeeters 1983 Relationship between galactinol synthase activity and sugar composition of leaves and seeds of several crop species. *Journal of American Society of Horticultural Science* 108 (4): 600–605.

Hattori, S and T. Shiroya 1951 The sugars in the seeds and seedlings of *Pinus thunbergii*. *Archives of Biochemistry and Biophysics* 34: 121–134.

Hurkman, W. J. and C. K. Tanaka 1996 Effect of salt stress on germin gene expression in barley roots. *Plant Physiology* 110 (3): 971–977.

Jacobsen, K. S., D. W. Hughes, and G. A. Galau 1994 Simultaneous induction of postabscission and germination mRNAs in cultured dicotyledonous embryos. *Planta* 192: 384–394.

Kao, C. 1973 Biochemical changes in seeds of Taiwan red pine and Chinese fir during germination. *Forest Science* 19 (4): 297–301.

Leprince, O., G. A. F. Hendry, and B. D. McKersie 1993 The mechanisms of desiccation tolerance in developing seeds. *Seed Science Research* 3: 231–246.

Lin, Tsan-Piao and N-H Huang 1994 The relationship between carbohydrate composition of some tree seeds and their longevity. *Journal of Experimental Botany* 45 (278): 1289–1294.

Murphy, J. B. and M. F. Hammer 1988 Respiration and soluble sugar metabolism in sugar pine embryos. *Physiologia Plantarum* 74: 95–100.

Pullman, G. S. and P. K. Gupta. 1991 Method for reproducing coniferous plants by somatic embryogenesis using absorbent materials in the development state media. U.S. Pat. No. 5,034,326.

Roberts, D. R. 1993 Process for production, desiccation and germination of conifer somatic embryos. U.S. Pat. No. 5,183,757.

Roberts, D. R., B. C. S. Sutton, B. S. Flynn 1990 Synchronous and high frequency germination of interior spruce somatic embryos following partial drying at high relative humidity. *Canadian Journal of Botaniy* 68: 1086–1090.

Steadman. K. J., H. W. Pritchard, and P. M. Dey 1996 Tissue-specific soluble sugars in seeds as indicators of storage category. *Annals of Botany* 77: 667–674.

Uddin, M. R. 1993 Somatic embryogenesis in gymnosperms. U.S. Pat. No. 5,187,092.

Wisniewski, M., T. J. Close, T. Artlip, and R. Arora 1996 Seasonal patterns of dehydrins and 70-kDa heat shock proteins in bark tissues of eight species of woody plants. *Physiologa Plantarum* 96 (3):496–505.

Wood, A. J. and P. B. Goldsbrough 1997 Characterization and expression of dehydrins in water stressed *Sorghum bicolor. Physiologia Plantarum* 99 (1): 144–152.

What is claimed is:

1. A method for evaluating biochemical maturity of conifer somatic enbryos which comprises determining content of sucrose series oligosaccharides in the somatic embryos and comparing the level measured with that of zygotic embryos at a similar development stage.

2. The method of claim 1 in which the conifers are selected from the genera Pseudotsuga and Pinus.

3. The method of claim 2 in which the conifers are from the genus Pinus.

4. The method of claim 3 in which the conifer is *Pinus taeda*.

5. The method of claim 2 in which the conifer is *Pseudotsuga menziesii*.

* * * * *